United States Patent
Higuchi et al.

(10) Patent No.: US 7,115,238 B2
(45) Date of Patent: Oct. 3, 2006

(54) CRYSTALLINE SILICOALUMINOPHOSPHATE SALT MOLECULAR SIEVE HAVING OCTAOXYGEN-MEMBERED RING PORE, PROCESS FOR PRODUCING THE SAME AND PROCESS FOR PRODUCING METHYLAMINE WITH THE MOLECULAR SIEVE AS CATALYST

(75) Inventors: Katsumi Higuchi, Ibaraki (JP); Akio Hashimoto, Ibaraki (JP); Toshihiro Nomura, Ibaraki (JP); Sachiko Arie, Ibaraki (JP); Takuo Ohshida, Ibaraki (JP); Takashi Kojima, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/515,380

(22) PCT Filed: May 23, 2003

(86) PCT No.: PCT/JP03/06477

§ 371 (c)(1),
(2), (4) Date: Mar. 10, 2005

(87) PCT Pub. No.: WO03/099720

PCT Pub. Date: Dec. 4, 2003

(65) Prior Publication Data

US 2005/0249661 A1    Nov. 10, 2005

(30) Foreign Application Priority Data

May 24, 2002  (JP) ............................. 2002-151551

(51) Int. Cl.
*B01J 29/85*   (2006.01)
*C01B 37/08*   (2006.01)
*C07C 209/00*  (2006.01)

(52) U.S. Cl. .............................. 423/306; 423/DIG. 30; 502/214; 564/479; 564/486

(58) Field of Classification Search ................ 423/305, 423/306, DIG. 30; 502/208, 214; 564/479, 564/486
See application file for complete search history.

(56) References Cited

U.S. PATENT DOCUMENTS 4,683,334 A    7/1987   Bergna et al.
5,443,812 A    8/1995   Nakajima et al.

FOREIGN PATENT DOCUMENTS

JP     8-310810 A      11/1996
JP     2000-117114 A    4/2000

*Primary Examiner*—David Sample
(74) *Attorney, Agent, or Firm*—Fitch, Even, Tabin & Flannery

(57) ABSTRACT

Problems on catalyst production and catalyst performance with respect to conventional 8-oxygen-membered ring micropore-containing crystalline silicoaluminophosphate molecular sieves as non-equilibrium methylamine synthesis catalysts, are resolved. A chabazite type crystalline silicoaluminophosphate molecular sieve having high purity and high crystallinity and having, on a crystal grain surface, an amorphous oxide layer whose Si/Al atomic ratio is greater than that of the whole crystal grain can be stably produced with high yield with the use of a small amount of structure directing agents by the present method characterized in that hydrothermal treatment conducted in the production of 8-oxygen-membered ring micropore-containing crystalline silicoaluminophosphate sieves is controlled under specified treating conditions. The thickness and composition of the amorphous oxide layer, which exert marked influence on the yield of dimethylamine synthesis, can be easily controlled and reproduced under the conditions of catalyst synthesis according to the invention. Thus, the catalyst of high performance can be stably supplied by the present invention at a low cost with reduced output of waste.

24 Claims, 2 Drawing Sheets

CRYSTALLINE SILICOALUMINOPHOSPHATE SALT MOLECULAR SIEVE HAVING OCTAOXYGEN-MEMBERED RING PORE, PROCESS FOR PRODUCING THE SAME AND PROCESS FOR PRODUCING METHYLAMINE WITH THE MOLECULAR SIEVE AS CATALYST

CROSS-REFERENCED APPLICATIONS

This application is the National Stage of International Application PCT/JP03/06477, filed May 23, 2003, the complete disclosure of which is incorporated herein by reference, which designated the U.S. and that International Application was not published under PCT Article 2 1(2) in English.

TECHNICAL FIELD

The present invention relates to an 8-oxygen-membered ring micropore-containing crystalline silicoaluminophosphate molecular sieve (hereinafter referred to as 8-membered ring SAPO in principle), a method for producing the same, and a method for producing methylamines with the thus-produced 8-membered ring SAPO as a catalyst.

More specifically, the present invention relates to an 8-membered ring SAPO having, on a crystal grain surface thereof, an amorphous oxide layer that has a great effect on catalyst performance, the amorphous oxide layer having an atomic ratio of silicon to aluminum (Si/Al) higher than the whole crystal grain, a method for producing the 8-membered ring SAPO which has the amorphous oxide layer, and a method for producing methylamines with the thus-produced 8-membered ring SAPO as a catalyst. Meanwhile, crystalline silicoaluminophosphate molecular sieve of chabazite structure is one of the 8-membered ring SAPOs that are mainly composed of silicon, aluminum, phosphorus and oxygen and have a CHA structure according to the IUPAC structural code specified by the International Zeolite Association (IZA).

Methylamines, in particular, dimethylamine, are important starting materials for solvents represented by dimethylformamide, rubber products, medicines and surfactants.

BACKGROUND ART

Methylamines are generally synthesized from methanol and ammonia at around 400° C. in the presence of a solid acid catalyst, e.g., silica-alumina. As is well known, use of the silica-alumina catalyst leads to predominant production of trimethylamine according to thermodynamic equilibrium although trimethylamine is least demanded among the three types of methylamines, namely, mono-, di- and tri-methylamines. Since dimethylamine accounts for most of the demand for methylamines, methods have been recently developed to selectively produce dimethylamine, overcoming the thermodynamic equilibrium composition.

Some of these methods include those using zeolites (crystalline aluminosilicate molecular sieves), e.g., Zeolite A (see, for example, Patent Document 1), FU-1 (see, for example, Patent Document 2), ZSM-5 (see, for example, Patent Document 3), ferrierite and erionite (see, for example, Patent Document 4), ZK-5, Rho, chabazite and erionite (see, for example, Patent Document 5) and mordenite (see, for example, Patent Documents 6, 7, 8 and 9).

These methods deal with zeolites small in micropore channel size, and try to improve selectivity for dimethylamine and catalytic activity by subjecting them to ion exchanging, dealumination, doping with a specific element or silylation in order to control micropore channel size or modify acid sites on external surfaces thereof.

Also known is a method for production of monomethylamine or the like at a higher proportion than the thermodynamically equilibrium composition by use of a crystalline silicoaluminophosphate molecular sieve (hereinafter referred to as SAPO in principle) as a non-zeolitic molecular sieve (see, for example, Patent Document 10).

After having extensively studied selective dimethylamine production techniques, the inventors of the present invention have also found that SAPOs modified with silica or other various oxides exhibit higher activity and dimethylamine selectivity than conventional zeolite catalysts, and have already applied for patents (see, for example, Patent Documents 11, 12 and 13).

It is generally considered that crystalline molecular sieves, e.g., zeolites and SAPOs, have a surface consisting of an exposed crystal lattice surface. Therefore, the surface of zeolites and SAPOs has strong acid sites which are characteristic of molecular sieves that contain silicon and aluminum. In order to improve selectivity for dimethylamine production, the surface acid sites are often subjected to chemical vapor deposition using silicon compounds, liquid-phase silylation, modification with a boron- or phosphorus-containing compound, or the like (see, for example, Patent Documents 14, 15, 16, 17 and 18). The techniques already described by the present inventors in the patent publications (see Patent Documents 11, 12 and 13) are also based on these concepts.

However, these conventional processes require lots of steps since they require separation and washing by centrifugation or filtration after synthesis of SAPOs and, in some cases, further modification of calcined catalysts. In particular, silylation needs precise control of moisture content of catalysts to be treated, and uses organic solvents, e.g., ethanol or toluene, thereby causing problems of disposal of waste fluid.

In this way, these conventional processes, in which synthesized SAPOs are further modified to improve activity and selectivity, involve problems to be solved both economically and environmentally. There are demands for development of new methods which can control activity and selectivity during steps for synthesis of SAPOs and thus differently from the conventional processes that require the post-treatment steps.

In order to solve these problems, the present inventors have already found that an 8-membered ring SAPO of chabazite structure having a rectangular parallelepiped or cubic crystal form of 5 μm or less in average grain diameter works as an excellent methylamine production catalyst of high activity and dimethylamine selectivity, and have already applied for patent (see Patent Document 19), in addition to the above-described techniques.

This 8-membered ring SAPO of chabazite structure exhibits excellent activity and selectivity without modification after synthesis. However, the present inventors have further studied it and observed a phenomenon of catalyst performance depending upon some synthesis lots. Therefore, it involves technical problems that must be further improved to obtain an optimum catalyst stably.

The 8-membered ring SAPO of chabazite structure having the above-described particle size and shape is synthesized using organic amines or organic ammonium salts, e.g., diethanolamine or tetraethyl ammonium hydroxide in an amount of 1.5±0.5 times the mole number of the aluminum compounds as $Al_2O_3$. On the other hand, the amount of the organic amine or organic ammonium salt incorporated into the 8-membered ring SAPO of chabazite structure just after synthesized but before calcined is an amount required to establish the crystalline structure, namely, only about 0.37 times the mole number as $Al_2O_3$. The surplus organic amines or organic ammonium salts, which are not incorporated into the crystalline structure, should be treated by activated sludge or the like. Therefore, synthesis of a pure 8-membered ring SAPO with a reduced amount of organic amines or organic ammonium salts would be a desirable process both economically and environmentally.

Since 8-membered ring SAPOs exhibit relatively high selectivity for dimethylamine in methylamine synthesis, various studies have conventionally been made on the synthesis of methylamines using such SAPOs (see, for example, Non-patent Document 4). As 8-membered ring SAPOs, are known SAPO-14, -17, -18, -33, -34, -35, -39, -42, -43, -44, -47 and -56 (see, for example, Non-patent Documents 5 and 6). Among them, three types, namely, SAPO-34, SAPO-44 and SAPO-47 are known to have the chabazite structure. In particular, the SAPO-34 of chabazite structure has been extensively studied as a catalyst for methylamine synthesis and methanol conversion (see, for example, Patent Documents 10 and 21).

It is known that these 8-membered ring SAPOs can be synthesized by hydrothermally treating a mixture of a silicon compound, aluminum compound, phosphorus compound and water in the presence of a structure directing agent such as tetraethyl ammonium hydroxide, morpholine, cyclohexylamine and diethylethanolamine (see, for example, Patent Document 20). It is not known, however, that these 8-membered ring SAPOs have an amorphous oxide layer on their crystal grain surfaces, and the amorphous oxide layer grows on crystal grain surfaces during the hydrothermal synthesis and has a great effect on yield and selectivity of the methylamine synthesis.

In general, the mixture to be hydrothermally treated to synthesize 8-membered ring SAPOs is represented by the compositional formula (1) shown below, and the structure directing agent R is used in an amount of 1 to 3 times the mole number of $Al_2O_3$ in the mixture (a/c=1 to 3):

$aR, bSiO_2, cAl_2O_3, dP_2O_5, eH_2O$      Formula (1)

Survey of the amount of structure directing agents used for synthesis of 8-membered ring SAPOs on various patent documents and literatures reveals that structure directing agents are used in an amount of at least one times the mole number of $Al_2O_3$ in the mixture to be hydrothermally treated, in order to produce 8-membered ring SAPOs of chabazite structure with high purity and high degree of crystallinity, and it is mentioned that, when they are used in a smaller amount, there occur impurities, e.g., a SAPO-5 structure which falls under the AFI structure according to the IUPAC structural code specified by the International Zeolite Association (IZA), as well as cristobalite or berlinite of aluminum phosphates.

A literature describes synthesis of SAPO-34 using tetraethyl ammonium hydroxide (TEAOH) as a structure directing agent (see, for example, Non-patent Document 1), and discusses that pure SAPO-34 is produced at a TEAOH/$Al_2O_3$ molar ratio of 2 to 3, SAPO-5 is produced at a ratio of 1 to 2, and a high-density phase is produced at a ratio below 1. It is also mentioned that grains having a non-crystalline amorphous structure are produced at a ratio above 3.

A literature describes synthesis of SAPO-34 using morpholine as a structure directing agent (see, for example, Non-patent Document 2), and discusses that a mixture of aluminum phosphate cristobalite and an amorphous compound is produced at a morpholine/$Al_2O_3$ molar ratio of 0.5 or less, a mixture of 80% SAPO-34 and 20% cristobalite is obtained at a morpholine/$Al_2O_3$ molar ratio of 1.0, and pure SAPO-34 is obtained at a morpholine/$Al_2O_3$ molar ratio of 2.0 or more.

In addition, a literature describes synthesis of SAPO-44 using cyclohexylamine as a structure directing agent (see, for example, Non-patent Document 3), and discusses that contamination with SAPO-5 occurs at a cyclohexylamine/$Al_2O_3$ molar ratio of 1.9 or less.

The above-cited references are as follows:

Patent Document 1: Japanese Patent Laid-Open No. S56-69846A,

Patent Document 2: Japanese Patent Laid-Open No. S54-148708A,

Patent Document 3: U.S. Pat. No. 4,082,805 specification,

Patent Document 4: Japanese Patent Laid-Open No. S56-113747A,

Patent Document 5: Japanese Patent Laid-Open No. S61-254256A,

Patent Document 6: Japanese Patent Laid-Open No. S56-46846A,

Patent Document 7: Japanese Patent Laid-Open No. S58-49340A,

Patent Document 8: Japanese Patent Laid-Open No. S59-210050A,

Patent Document 9: Japanese Patent Laid-Open No. A59-227841A,

Patent Document 10: Japanese Patent Laid-Open No. H02-734A,

Patent Document 11: Japanese Patent Laid-Open No. H11-35527A,

Patent Document 12: Japanese Patent Laid-Open No. H11-239729A,

Patent Document 13: Japanese Patent Laid-Open No. 2000-5604A,

Patent Document 14: Japanese Patent Laid-Open No. H03-262540A,

Patent Document 15: Japanese Patent Laid-Open No. H 11-508901A,

Patent Document 16: Japanese Patent Laid-Open No. H06-179640A,

Patent Document 17: Japanese Patent Laid-Open No. H07-2740A,

Patent Document 18: Japanese Patent Laid-Open No. S61-254256A,

Patent Document 19: Japanese Patent Laid-Open No. 2000-117114A,

Patent Document 20: U.S. Pat. No. 4,440,871 specification,

Patent Document 21: U.S. Pat. No. 5,126,308 specification,

Non-Patent Document 1: J. Liang, H. Li, S. Zhao, W. Guo, R. Wang, and M. Ying, Appl. Catal., 1991, 64, pp. 31 to 40, Non-Patent Document 2: A. M. Prakash, S. Unnikrishnan, J. Chem. Soc. Faraday Trans., 1994, 90 (15), pp. 2291 to 2296, Non-Patent Document 3: S. Ashtekar, S. V. V. Chilukuri, D. K. Chakrabarty, J. Phys. Chem., 1994, 98, pp. 4878 to 4883, Non-Patent Document 4: D. R. Corbin, S. Schwarz, and G. C. Sonnichsen, Catalysis Today, 1997, 37, pp. 71 to 102, Non-Patent Document 5: E. M. Flanigen, B. M. Lok, R. L. Patton, and S. T. Wilson, New Developments in Zeolite Science and Technology, Elsevier, 1986, pp. 103 to 112, and Non-Patent Document 6: Structure Commission of the International Zeolite Association, Atlas of Zeolite Framework Types, Elsevier, 2001, pp. 14 to 15.

As described above, the present inventors have found that, among the SAPOs, an 8-membered ring SAPO of chabazite structure having a rectangular parallelepiped or cubic crystal form of 5 μm or less in average grain diameter works as an excellent methylamine production catalyst high in activity and dimethylamine selectivity without any modification after synthesis, and have already applied for patent (Japanese Patent Laid-Open No. 2000-117114A). However, it has been observed that the SAPO having the above grain diameter and shape still shows variation of catalyst performance depending upon production lots.

The above-described 8-membered ring SAPO of chabazite structure is obtained by hydrothermally treating a starting mixture that contains organic amines or organic ammonium salts such as tetraethyl ammonium hydroxide (TEAOH) and diethanolamine in an amount of 1.5±0.5 times the mole number of aluminum compounds as $Al_2O_3$. However, such a method as described above, in which an excessive amount of organic amines or ammonium salts is required, produces the catalyst at a low yield and needs treatment of the surplus organic amines or ammonium salts by activated sludge or the like.

Therefore, the SAPO disclosed in Japanese Patent Laid-Open No. 2000-117114A involves problems that must be further improved concerning catalytic stability for amine synthesis, the excess amount of structure directing agents, or the like.

Objects of the present invention are to solve the above problems and provide an 8-membered ring SAPO having excellent catalytic activity and dimethylamine selectivity, a method for stably producing the SAPO at a low cost, and a method for producing methylamines in the presence of the SAPO as a catalyst.

DISCLOSURE OF INVENTION

As a result of intensive researches for solving the above problems, the present inventors have found that an 8-membered ring SAPO having a body of a crystalline molecular sieve grain which is formed therearound with an amorphous oxide layer having a silicon/aluminum (Si/Al) atomic ratio higher than the crystalline portion is obtained with the Si/Al atomic ratio of the amorphous oxide layer being higher than the Si/Al atomic ratio of the whole crystal grain, during a synthesis step of the 8-membered ring SAPO, and also have found that the Si/Al atomic ratio or thickness of the amorphous oxide layer has a great effect on catalytic activity and dimethylamine selectivity, and can be precisely controlled by temperature and time of the hydrothermal treatment conducted during a step for forming the amorphous oxide layer. It is also found that a catalyst stable in activity and dimethylamine selectivity can be produced by the technique for controlling the Si/Al atomic ratio or thickness of the amorphous oxide layer.

It is also found that the hydrothermal treatment comprising a step for hydrothermal treatment at 80 to 130° C. for 1 hour or more and then at 150 to 200° C. for 1 to 10 hours (first step) and a step for hydrothermal treatment at 150 to 200° C. for 10 hours or more (second step) produces a pure 8-membered ring SAPO high in degree of crystallinity, and gives higher yield of catalysts than conventional processes, even when the amount of organic amines or organic ammonium salts used as structure directing agents is reduced to below 1.0 in terms of molar ratio to $Al_2O_3$.

It is also found that the 8-membered ring SAPO thus produced has higher catalytic activity and dimethylamine selectivity than the SAPOs of chabazite structure obtained by conventional processes. And, the present inventors have established a method for stably producing a catalyst excellent in activity and dimethylamine selectivity by combining the technique for producing the 8-membered ring SAPO with the technique for controlling the Si/Al atomic ratio or thickness of the amorphous oxide layer, thereby achieving the present invention.

That is, the present invention relates to an 8-membered ring SAPO having an amorphous oxide layer on a crystal grain surface thereof, the amorphous oxide layer having a higher Si/Al atomic ratio than the whole crystal grain thereof, and to a method for producing an 8-membered ring SAPO characterized in that thickness of the amorphous oxide layer or surface composition of the crystal grain is precisely controlled by temperature and time of hydrothermal treatment conducted during a step for forming the amorphous oxide layer. The present invention also relates to a method for producing an 8-membered ring SAPO by hydrothermally treating a starting mixture comprising an organic amine and/or organic ammonium salt as a structure directing agent together with an aluminum compound, phosphorus compound, silicon compound and water, wherein a ratio of the total mole number of the organic amine and organic ammonium salt to the mole number of the aluminum compound as $Al_2O_3$ is 0.4 to 0.98, and the starting mixture is subjected to treatment which comprises a first step of a hydrothermal treatment at 80 to 130° C. for 1 hour or more followed by a further hydrothermal treatment at 150 to 200° C. for 1 to 10 hours, and a second step of a hydrothermal treatment at 150 to 200° C. for 10 hours or more. The present invention also relates to a method for producing methylamines, in which the 8-membered ring SAPO produced by combination of the above-described techniques for production of the 8-membered ring SAPO is used as a catalyst.

More specifically, the present invention relates to an 8-membered ring SAPO, methods for producing the SAPO, and methods for producing methylamines by use of the 8-membered ring SAPO as a catalyst, as described in (1) to (24) below.

(1) An 8-membered ring SAPO which comprises an amorphous oxide layer on a crystal grain surface thereof, wherein the amorphous oxide layer has a higher atomic ratio of silicon to aluminum than the whole crystal grain thereof.

(2) The 8-membered ring SAPO as defined in (1), wherein the whole crystal grain has an atomic ratio of silicon to aluminum in a range of 0.05 to 0.30, and the amorphous oxide layer on the crystal grain surface has an atomic ratio of silicon to aluminum of 0.50 or more, as determined by X-ray photoelectron spectroscopy.

(3) The 8-membered ring SAPO as defined in any one of (1) and (2), wherein the amorphous oxide layer on the crystal grain surface has an atomic ratio of silicon to phosphorus of 0.55 or more as determined by X-ray photoelectron spectroscopy.

(4) The 8-membered ring SAPO as defined in any one of (1) to (3), wherein the amorphous oxide layer on the crystal grain surface has a thickness in a range of 3 to 20 nm.

(5) The 8-membered ring SAPO as defined in any one of (1) to (4), which further comprises at least one element selected from the group consisting of magnesium, yttrium, titanium, zirconium, manganese, iron, cobalt and tin.
(6) The 8-membered ring SAPO as defined in any one of (1) to (5), wherein the crystal grain has a rectangular parallelepiped and/or cubic form, and an average grain diameter of 5 μm or less.
(7) The 8-membered ring microporous SAPO as defined in any one of (1) to (6), which has a crystal grain body portion that is the whole crystal grain from which the amorphous oxide layer on the crystal grain surface is excluded, said crystal grain body portion being of chabazite structure.
(8) The 8-membered ring SAPO of chabazite structure as defined in (7), which has a ratio of peak intensity at (100) plane of AFI structure to peak intensity at (100) plane of chabazite structure, this ratio being 0.02 or less as determined by X-ray diffractometry.
(9) A method for producing the 8-membered ring SAPO defined in any one of (1) to (8) by hydrothermally treating a starting mixture composed of an organic amine and/or organic ammonium salt together with an aluminum compound, phosphorus compound, silicon compound and water to produce the 8-membered ring SAPO having an amorphous oxide layer on a crystal grain surface thereof, which comprises a first step for producing at least a crystalline portion thereof and a second step for conducting hydrothermal treatment to form the amorphous oxide layer on the crystal grain surface.
(10) The method for producing the 8-membered ring SAPO, as defined in (9), wherein the first step comprises two sub-steps for hydrothermal treatment, one being a step for carrying out hydrothermal treatment at 80 to 130° C. for 1 hour or more, and the other being a step for carrying out hydrothermal treatment at 150 to 200° C. for 1 to 10 hours.
(11) The method for producing the 8-membered ring SAPO, as defined in (10), wherein the sub-step of the first step for carrying out hydrothermal treatment at 80 to 130° C. for 1 hour or more includes a step in which temperature is increased from 80 to 130° C. in 1 hour or more, or a step in which temperature is kept at a constant level in a range of 80 to 130° C. for 1 hour or more.
(12) The method for producing the 8-membered ring SAPO, as defined in any one of (9) to (11), wherein the second step for hydrothermal treatment includes a step for carrying out hydrothermal treatment at 150 to 200° C. for 10 hours or more.
(13) The method for producing the 8-membered ring SAPO, as defined in (9), wherein the first step comprises two sub-steps, one being a step for carrying out hydrothermal treatment at a constant temperature in a range of 95 to 125° C. for 3 to 24 hours and the other being a step for carrying out hydrothermal treatment at 150 to 200° C. for 1 to 10 hours, and the second step for hydrothermal treatment comprises a step for carrying out hydrothermal treatment at 150 to 200° C. for 10 to 150 hours.
(14) The method for producing the 8-membered ring SAPO, as defined in any one of (9) to (13), wherein the starting mixture composed of an organic amine and/or organic ammonium salt together with an aluminum compound, phosphorus compound, silicon compound and water has a ratio of the total mole number of the organic amine and organic ammonium salt to the mole number of the aluminum compound as $Al_2O_3$, this ratio being 0.4 to 0.98.
(15) The method for producing the 8-membered ring SAPO, as defined in any one of (9) to (14), wherein the organic amine and/or organic ammonium salt is tetraethyl ammonium hydroxide.
(16) The method for producing the 8-membered ring SAPO, as defined in any one of (9) to (15), wherein the aluminum compound is pseudoboehmite.
(17) The method for producing the 8-membered ring SAPO, as defined in any one of (9) to (16), wherein the phosphorus compound is phosphoric acid.
(18) The method for producing the 8-membered ring SAPO, as defined in any one of (1) to (17), wherein the silicon compound is silica sol.
(19) The method for producing the 8-membered ring SAPO, as defined in any one of (1) to (18), wherein a silicon compound is further added before or during the second step.
(20) The method for producing the 8-membered ring SAPO, as defined in any one of (9) to (19), wherein at least one element selected from the group consisting of magnesium, yttrium, titanium, zirconium, manganese, iron, cobalt and tin is further added.
(21) The method for producing the 8-membered ring SAPO, as defined in any one of (9) to (20), wherein the 8-membered ring SAPO is of chabazite structure.
(22) A method for producing methylamines, comprising reacting methanol and ammonia in the presence of the 8-membered ring SAPO defined in any one of (1) to (8).
(23) A method for producing methylamines, comprising reacting methanol and monomethylamine in the presence of the 8-membered ring SAPO defined in any one of (1) to (8).
(24) A method for producing methylamines, comprising carrying out disproportionation reaction of monomethylamine in the presence of the 8-membered ring SAPO defined in any one of (1) to (8).

Hereinafter, the present invention is described in more detail. The SAPO of the present invention is an 8-membered ring SAPO having an amorphous oxide layer on a surface thereof, the oxide layer having a higher Si/Al atomic ratio than the whole crystal grain.

SAPO means a crystalline and microporous compound having a three-dimensional, microporous, crystalline framework structure that is composed of a tetrahedron unit of $PO_2^+$, $AlO_2^-$ and $SiO_2$, as described in U.S. Pat. No. 4,440,871 specification.

Moreover, a compound containing a tetrahedron unit having metal(s) other than silicon, aluminum and phosphorus in its three-dimensional, microporous, crystalline framework structure is disclosed in EP 159,624 or the like. It is referred to as ELAPSO molecular sieve. However, these patent documents are silent on SAPOs having an amorphous oxide layer on the surface thereof as provided by the present invention.

The 8-membered ring SAPO of the present invention may contain a metallic component other than silicon, aluminum and phosphorus. It preferably contains an element selected from magnesium, yttrium, titanium, zirconium, manganese, iron, cobalt and tin, of which titanium and zirconium are particularly preferable for their effects of improving catalytic activity and life. These elementary components may be present in and/or outside the three-dimensional, microporous, crystalline framework structure. Content of these elements is not limited, but their total content is preferably in an atomic ratio of 0.0001 to 0.1 to aluminum. The 8-membered ring SAPO containing these elements can be prepared by hydrothermally treating a mixture comprising a structure directing agent, silicon compound, aluminum compound, phosphorus compound, water, and nitrate, sulfate, chloride, oxide sol, oxide powder, alkoxide and/or complex of the above-described element(s).

The SAPO preferably has an effective micropore size in a range from 0.3 to 0.6 nm, in order to produce methylamines, in particular, produce dimethylamine selectively, by the reaction of methanol and ammonia. Such micropores prevent trimethylamine molecules from passing therethrough, but allow smaller monomethylamine and dimethylamine molecules to pass therethrough, thereby finally slanting reaction selectivity towards monomethylamine and dimethylamine (D. R. Corbin, S. Schwarz, and G. C. Sonnichsen, Catalysis Today, 37 (1997), pp. 71 to 102). The above-described effective micropore size corresponds to those of 8-oxygen- to 10-oxygen-membered ring SAPOS, of which the 8-membered ring SAPO is necessary to further decrease trimethylamine selectivity.

Examples of 8-membered ring SAPOs include SAPO-14, -17, -18, -33, -34, -35, -39, -42, -43, -44, -47 and -56. The relationship between the number attached to each of these SAPOs and IUPAC structural code specified by the Structure Commission of the International Zeolite Association (IZA), is described in, for example, "Atlas of Zeolite Framework Types" edited by Structure Commission of the International Zeolite Association, published by Elsevier. The above-described SAPOs correspond to the IUPAC structural codes of AFN, ERI, AEI, ATT, CHA, LEV, ATN, LTA, GIS, CHA, CHA and AFX, respectively. Of these SAPOs, SAPO-17, -18, -34, -35, -44, -47 and -56 are preferable, and SAPO-34 of chabazite structure is particularly preferable.

The 8-membered ring SAPO of chabazite structure according to the present invention is a crystalline molecular sieve of CHA structure according to the IUPAC structural code specified by the International Zeolite Association (IZA) and mainly composed of silicon, aluminum, phosphorus and oxygen. More specifically, it is a compound having a structure represented by CHA, among the SAPOs described in U.S. Pat. No. 4,440,871 specification. As SAPOs having such CHA structure, known are three types of SAPOS, namely, SAPO-34, SAPO-44 and SAPO-47, as described in M. Flanigen, R. L. Patton, and S. T. Wilson, Studies in Surface Science and Catalysis, Innovation in Zeolite Materials Science, pp. 13 to 27, 1988.

The 8-membered ring SAPO of the present invention is most featured in that it has, on a surface thereof, an amorphous oxide layer having a higher Si/Al atomic ratio than the whole crystal grain. The amorphous oxide layer can be observed by FIB-STEM analysis. For example, FIGS. 1 and 2 show the SAPO-34, where a cubic SAPO-34 grain was scraped off on both sides by focused ion beams (FIB, FB-2100 manufactured by Hitachi Ltd.) and the cross section of the remaining 80 nm thick flake was observed by a scanning transmission electron microscope (STEM, thin film evaluation device HD-2000 manufactured by Hitachi Ltd.). FIG. 1 shows a 3-layered structure, where the outermost layer is of carbon, platinum and tungsten deposited to fix the sample grain and increase its electroconductivity. The central portion is the crystal grain body, and a thin film between them is the amorphous oxide layer. FIG. 2 shows the grain of FIG. 1 magnified for the portion of around 100 nm deep from the surface. The portion with a check pattern corresponds to the crystal grain body stripped of the amorphous oxide layer, and the white layer having no check pattern corresponds to the amorphous oxide layer. The check pattern indicates that the grain has a regular structure, and the clear Laue spots observed by electron beam diffractometry indicate that the crystal grain body portion is crystalline (FIG. 3). On the other hand, the white layer showing no check pattern indicated no Laue spots according electron beam diffraction analysis, and thus it lacks a regular structure and is amorphous (FIG. 4). Moreover, the amorphous layer is a silicon-rich oxide layer having a higher Si/Al atomic ratio than the crystal grain body, as confirmed by the compositional analysis using an energy dispersive X-ray (EDX) analyzer.

Existence of the amorphous oxide layer and its thickness greatly affect reactivity and dimethylamine selectivity in the production of methylamines by the reaction of methanol and ammonia, or disproportionation reaction of monomethylamine. Taking the above-described SAPO-34 as an example, the SAPO-34 having an amorphous oxide layer thinner than 3 nm achieves a reaction at a high reactivity but produces trimethylamine at a selectivity of 10% or higher, and thus shows insufficient dimethylamine selectivity. The SAPO-34 having an amorphous oxide layer thicker than 20 nm, on the other hand, shows a low trimethylamine selectivity of 1% or less but insufficient reactivity. These results can be explained by considering that the thin amorphous oxide layer does not sufficiently cover active acid sites that exist on the crystal grain surface and have no molecular sieve effect, and the remaining active acid sites produce trimethylamine that is most stable thermodynamically, whilst the excessively thick amorphous oxide layer sufficiently covers active acid sites, but retards the diffusion of reacting species towards active sites of the crystal grain body or the dissociation of the produced species from the crystal body, thereby lowering reactivity. Since the amorphous oxide layer is mainly composed of oxides of silicon, aluminum and phosphorus and contains silicon as a major component, it lacks strong acidity unlike silica-alumina and thus shows little reactivity.

Therefore, preferable thickness of the amorphous oxide layer in the present invention is 3 to 20 nm, more preferably 3.5 to 16 nm.

Composition of the amorphous oxide layer can be analyzed by the above-described energy dispersive X-ray analyzer, and more simply determined by analysis of the surface composition of the crystal grain according to X-ray photoelectron spectroscopy (XPS, ESCA). The X-ray photoelectron spectroscopy can determine the composition of a depth of 1.5 to 4.0 nm from the outermost surface of crystal grains.

Composition of the crystal grain body, on the other hand, can be considered to be almost the same as that of the whole crystal grain, because the amorphous oxide layer is very thin. For example, it can be determined by completely dissolving SAPO grains in a mineral acid or the like and using inductively coupled plasma emission spectroscopy (ICP).

The surface composition according to the present invention was determined by the ESCALAB MKII analyzer manufactured by VG Scientific Ltd. with Al-Kα ray as the X-ray source (1486.7 eV) using Scofield correction factors as described in J. H. Scofield, Journal of Electron Spectroscopy and Related Phenomena, 8 (1976), pp. 129 to 137. Composition of the whole crystal grain was determined by dissolving SAPOs in a low-concentration hydrofluoric acid solution using the SPS-1200VR analyzer manufactured by Seiko Instruments Inc.

Surface composition of the crystal grain, determined by X-ray photoelectron spectroscopy, changes with thickness of the amorphous oxide layer, and Si/Al and Si/P atomic ratios increase with the thickness of the amorphous oxide layer. In the case of the SAPO-34, for example, the Si/Al and Si/P atomic ratios determined by X-ray photoelectron spectroscopy are respectively 0.49 and 0.53 when thickness of the amorphous oxide layer is 2.5 nm; the Si/Al and Si/P atomic ratios are respectively 1.61 and 2.45 when the thickness is 7 nm; and the Si/Al and Si/P atomic ratios are respectively 1.98 and 2.92 when the thickness is 13 nm.

The increase in Si/Al and Si/P atomic ratios with the increase in the thickness of the amorphous oxide layer results from the silicon component that preferentially deposits onto the crystal grain surface from the synthesis solution containing silicon, aluminum and phosphorus components, during the amorphous oxide layer forming process described later. This is supported by the fact that concentration of silicon components in the synthesis solution selectively decreases when the solution is analyzed by ICP during the amorphous oxide layer forming process.

In other words, surface composition of the crystal grain corresponds to thickness of the amorphous oxide layer. An 8-membered ring SAPO exhibiting excellent reactivity and dimethylamine selectivity has, on the surface thereof, a Si/Al atomic ratio in a range from 0.50 to 2.20, when no silicon compound is added in the below-described second step. Similarly, the surface Si/P atomic ratio is in a range from 0.55 to 3.10. When a silicon compound is added in the second step, silicon components are present in the synthesis solution at a fairly higher concentration than the aluminum and phosphorus components. In this case, an 8-membered ring SAPO exhibiting excellent performance has, on the surface thereof, Si/Al and Si/P atomic ratios of 0.50 or more and 0.55 or more, respectively.

The whole 8-membered ring SAPO generally has an ICP-determined Si/Al atomic ratio in a range from 0.05 to 0.30, although the atomic ratio varies depending on synthesis conditions.

As discussed above, the Si/Al atomic ratio of the crystal grain surface of the 8-membered ring SAPO of the present invention, which is determined by X-ray photoelectron spectroscopy with Al-K$\alpha$ ray (1486.7 eV) as the X-ray source, is higher than the Si/Al atomic ratio of the whole crystal grain, which is determined by the ICP analysis, and the former Si/Al atomic ratio is preferably 0.50 or more, more preferably 0.50 to 2.20. On the other hand, the Si/P atomic ratio of the crystal grain surface, determined by X-ray photoelectron spectroscopy, is preferably 0.55 or more, more preferably 0.55 to 3.10. The Si/Al atomic ratio of the whole crystal grain of the 8-membered ring SAPO of the present invention is preferably in a range from 0.05 to 0.30.

In the present invention, the amorphous oxide layer is mainly composed of oxides of silicon, aluminum and phosphorus, but may contain elements other than silicon, aluminum and phosphorus.

The amorphous oxide layer is formed after crystallization of the SAPO crystal grain body is almost completed. In other words, the SAPO of the present invention with an amorphous oxide layer on a surface thereof is synthesized by way of two steps, namely, a first step in which a starting mixture comprising an organic amine and/or organic ammonium salt together with an aluminum compound, a phosphorus compound, a silicon compound and water is hydrothermally treated to produce at least crystalline portions of the SAPO, and a second step wherein a further hydrothermal treatment is carried out to form the amorphous oxide layer on a surface of the crystal grain.

More specifically, the first step is a step for crystallizing most of the starting mixture in the very commonly-known production process of 8-membered ring SAPOs, and the second step is a step in which the 8-membered ring SAPO thus crystallized in the first step is further treated hydrothermally in a silicon-containing solution.

In the present method for producing an 8-membered ring SAPO as described later, the first step corresponds to the process in which hydrothermal treatment is carried out at 80 to 130° C. for 1 hour or more while crystallization does not proceed substantially, and then further hydrothermal treatment is carried out at 150 to 200° C. for 1 to 10 hours so as to allow crystallization to notably proceed. On the other hand, the second step corresponds to the subsequent process in which further hydrothermal treatment is carried out at 150 to 200° C. after 8-membered ring SAPOs have been crystallized by the hydrothermal treatment carried out at 150 to 200° C. for 1 to 10 hours.

Thickness and surface composition of the amorphous oxide layer can be controlled by conditions of hydrothermal treatment in the second step. Thickness of the amorphous oxide layer increases as time of hydrothermal treatment increases, e.g., 2.5 nm in 5 hours, 7 nm in 50 hours, 13 nm in 100 hours and 25 nm in 175 hours in the case of the above-described SAPO-34 hydrothermally treated at 170° C. Rate at which the amorphous oxide layer is formed also depends on temperature of hydrothermal treatment. By utilizing such characteristics, e.g., by changing temperature and/or time of hydrothermal treatment, thickness and surface composition of the amorphous oxide layer can be controlled. Moreover, thickness or surface composition of the amorphous oxide layer may be analyzed with lapse of time, so that the thickness or surface composition is controlled to suit a reaction, e.g., the reaction of methanol and ammonia for producing methylamines.

The temperature and time of hydrothermal treatment in the second step is not limited, because once the 8-membered ring SAPO crystal grains are formed by hydrothermal treatment in the first step, formation of the amorphous oxide layer proceeds even at room temperature, although slowly, by keeping these grains in the synthesis solution even after the solution is cooled to room temperature. However, the hydrothermal treatment in the second step is preferably carried out at 150 to 200° C. for 10 hours or more from practical viewpoint.

The rate at which the amorphous oxide layer is formed can be controlled by concentration of silicon compounds in the synthesis solution, besides the above-described temperature and time of hydrothermal treatment. In the present invention, therefore, a silicon compound may be further added before or during the second step. The addition of a silicon compound is particularly preferable when the amorphous oxide layer is formed slowly. The silicon compound that can be used includes powdered silica, silica sol, orthosilicate or the like, of which silica sol is particularly preferable. Moreover, a compound containing another element, e.g., yttrium, titanium, zirconium, iron or tin, may be used, as required, in addition to a silicon compound.

As described in Background Art, crystalline molecular sieves having a pure silica layer around the SAPO body are well known, which include, for example, ammonium type mordenite treated with tetrachlorosilane in gas phase as disclosed in Japanese Patent Laid-open No. H11-508901A, and mordenite or SAPO silylated with an organic silicon compound in liquid phase as disclosed in Japanese Patent Laid-open Nos. H07-2740A and H11-35527A.

However, the structure of the surface silica layer of these SAPOs has been little investigated. M. Niwa and Y. Murakami (J. of Chem. Soc. of Japan, pp. 410 to 419, 1989) consider that tetrahedral structures of silica are regularly arranged on an exposed regular structure of SAPO so that a structure similar to a crystalline molecular sieve body is formed (epitaxy growth of silica). More recently, D. Lu, J. Nomura, K. Domen, H. A. Begum, N. Katada and M. Niwa (Shokubai-shi, Vol. 44, pp. 483 to 485, 2002) have observed a vapor-deposited silica layer by transmission electron microscopy and have mentioned that the silica layer is not amorphous but has a regular structure growing under limitation by an external surface structure of zeolite. These known silica layers growing by modification with silicon compounds are considered to be crystalline, and different from the amorphous oxide layer of the present invention.

Moreover, in these conventionally-known methods, particularly, those employing a gas-phase process, the silica layer is produced by way of a number of steps and complicated precise control, e.g., drying of crystalline molecular sieves under restricted conditions, treatment with tetrachlorosilane under specific conditions and washing and elimination of chlorine components resulting from the treatment. Also, the silylation in liquid phase needs fine control techniques and a number of steps for controlling moisture content of crystalline molecular sieves and surface-treating crystalline molecular sieves based on hydrolysis of organic silicon compounds. In contrast, since the present invention forms the amorphous oxide layer during the 8-membered ring SAPO synthesis process, it needs a much smaller number of steps than conventional methods, and thus can control catalyst performance very simply and hence is economical.

In other words, it has not been known at all that an amorphous oxide layer is present on a surface of a synthesized 8-membered ring SAPO grain, existence and thickness of the amorphous oxide layer have a great effect on catalyst performance, and the thickness of the amorphous oxide layer can be precisely controlled by conditions of hydrothermal treatment in the course of formation of the amorphous oxide layer in the 8-membered ring SAPO synthesis process. The 8-membered ring SAPO of the present invention, which has the amorphous oxide layer on a surface thereof, is completely different, both in concept and essence, from the silica-modified crystalline molecular sieves such as silica-modified SAPOs that have been silylated in liquid phase.

Referring to conditions of hydrothermal treatment according to the present invention, the hydrothermal treatment as the first step is carried out by hydrothermally treating a starting mixture at 80 to 130° C. for 1 hour or more under which no crystallization of the 8-membered ring SAPO proceeds substantially, and then hydrothermally treating it at 150 to 200° C. so as to allow the crystallization to notably proceed, and the hydrothermal treatment as the second step is subsequently carried out by performing hydrothermal treatment at 150 to 200° C. This make it possible to stably produce an 8-membered ring SAPO which is high in purity and degree of crystallinity, has an amorphous oxide layer of controlled Si/Al molar ratio and thickness, and is excellent in catalytic activity and dimethylamine selectivity even when a structure directing agent is used in an amount lower than conventional processes, for example, in an amount of less than 1.0 times the mole number of $Al_2O_3$. In other words, since the first step comprises a step of hydrothermal treatment conducted under relatively mild temperature conditions of 80 to 130° C. for 1 hour or more so as to effectively utilize the structure directing agent, it has been made possible to reduce the amount of the structure directing agent close to the minimum amount that will be actually incorporated into the crystal.

The production method of the present invention is further featured in that catalyst yield increases as the addition amount of structure directing agents decreases. Because of the two advantages, namely, the reduced amount of the structure directing agent and the increased yield of catalyst, the method of the present invention increases catalyst production drastically compared with conventional methods, and thus greatly lowers costs for production of catalyst and is quite advantageous in terms of industrial production. Therefore, compared with conventional processes requiring an excessive amount of structure directing agents, the production method of the present invention is greatly improved from economical viewpoints since it reduces not only costs for consumption and disposal of structure directing agents but also costs for catalyst production thanks to the increased yield of catalyst.

The reason why the present method improves the catalyst yield can be explained as follows. That is, conventional methods need a large amount of structure directing agent which is alkaline and invariably increases the pH level of the starting mixture. This increases solubility of the SAPO components, e.g., silicon, aluminum and phosphorus compounds, and thus decreases catalyst yield. The pH level after hydrothermal treatment was 8 or more according to conventional methods, but is generally 5.5 to 7.5 according to the present production method.

The 8-membered ring SAPO is generally synthesized by using a compound such as tetraethyl ammonium hydroxide, morpholine, cyclohexylamine and diethylethanolamine as a structure directing agent, mixing the structure directing agent together with a silicon compound, an aluminum compound, a phosphorus compound and water uniformly, and subjecting the mixture to hydrothermal treatment in an autoclave at a temperature of 150 to 200° C. for several to 200 hours.

$$aR, bSiO_2, cAl_2O_3, dP_{2I\ O5}, eH_2O \quad \text{Formula (1)}$$

The structure directing agent is generally used in an amount of one to three times the mole number of $Al_2O_3$, provided that the starting mixture to be hydrothermally treated is represented by the above compositional formula (1).

As described in Background Art, it was considered to be difficult to synthesize a pure 8-membered ring SAPO using a structure directing agent in an amount of less than one times the mole number of $Al_2O_3$, and no successful synthesis has been known. In addition to the patent documents cited before, a method for synthesis of a SAPO for use in production of olefins from methanol is described, for example, in U.S. Pat. No. 5,126,308, where the total addition amount of tetraethyl ammonium hydroxide and di-n-propylamine as structure directing agents is 1.0 or more times the mole number of $Al_2O_3$. U.S. Pat. No. 5,663,471 describes a SAPO production method, where the addition amount of tetraethyl ammonium hydroxide as a structure directing agent is 2.0 times the mole number of $Al_2O_3$.

The 8-membered ring SAPO includes molecules of structure directing agents in its micropores before being calcined. Amount of the structure directing agent present in the micropores can be determined by subjecting the SAPO to compositional analysis such as ICP, gravimetric analysis such as TG or LOI (loss on ignition) analysis, before the SAPO is calcined. L. Marchese, A. Frache, E. Gianotti, G. Marta, M. Causa and S. Coluccia (Microporous, and Mesoporous Materials, 30, 1999, pp. 145 to 153) describe synthesis of SAPO-34 in the presence of morpholine as a structure directing agent, and mention that SAPO-34 includes 1.5 molecules of the structure directing agent in the cage thereof before being calcined. This corresponds to a molar ratio of 0.49 to $Al_2O_3$. It is desirable to synthesize a pure 8-membered ring SAPO using the structure directing agent in this molar ratio of 0.49, but no example thereof has been known.

If synthesis is carried out as in Comparative Examples 1 to 3 in the below-described Examples section using a structure directing agent in a reduced amount of less than 1.0 times the mole number of $Al_2O_3$ under the conventional hydrothermal conditions in place of the present hydrothermal treatment carried out at 80 to 130° C. for 1 hour or more, there are produced not only an 8-membered ring SAPO but also non-8-membered ring ones such as SAPO-5 having an AFI structure and a structure falling under an aluminum phosphate of JCPDS card No. 20-0045 specified by International Centre for Diffraction Data. As a result, the produced 8-membered ring SAPO is decreased in purity and degree of crystallinity.

It is not clear why an 8-membered ring SAPO of high purity and crystallinity can be stably produced using a structure directing agent in a molar ratio of below 1.0 to $Al_2O_3$ when the first step includes a hydrothermal treatment carried out at 80 to 130° C. for 1 hour or more. For example, in case of 8-membered ring SAPOs of chabazite structure, it may be considered as follows.

When the hydrothermal treatment is carried out at 80 to 130° C. for 1 hour or more in the first step, there are formed double-six-ring-structure units constituting the framework of the 8-membered ring SAPO of chabazite structure, and nuclei of the 8-membered ring SAPO of chabazite structure in the synthesis solution. Thus, it is considered that crystallization of the 8-membered ring SAPO of chabazite structure proceeds fast when the subsequent hydrothermal treatment is carried out at 150 to 200° C.

In contrast, it is considered that, when the step of carrying out the hydrothermal treatment at 80 to 130° C. for 1 hour or more is omitted, the double-six-ring-structure units and the nuclei of the 8-membered ring SAPO of chabazite structure are formed insufficiently in the synthesis solution, and thus non-8-membered ring SAPOs such as a SAPO having the AFI structure is formed, or crystallization does not proceed completely, even when the solution is hydrothermally treated at 150 to 200° C. Such a phenomenon would hardly occur in the presence of a sufficient amount of the structure directing agent, but will become more noted as the amount of the structure directing agent is decreased.

Purity of the 8-membered ring SAPO can be determined by X-ray diffractometry. For example, purity of an 8-membered ring SAPO of chabazite structure can be estimated by the ratio of peak intensity at (100) plane of AFI structure to peak intensity at (100) plane of chabazite structure, determined by X-ray diffractometry. The peaks of chabazite structure and AFI structure at the (100) plane respectively appear at around 9.5° and around 7.4° in terms of 2θ according to the scanning axis 2θ/θ method with CuKα ray.

The 8-membered ring SAPO has an effective micropore diameter of around 4 Å, and thus trimethylamine whose molecular size is 6.3×5.8×4.1 Å cannot pass through the micropores in the synthesis of methylamines by the reaction of methanol and ammonia. Therefore, the 8-membered ring SAPO has a characteristic of selectively producing dimethylamine which is useful as a starting material for solvents, medicines, surfactants and so on. By contrast, SAPO-5, which is not of 8-membered ring but AFI structure, has an effective micropore diameter of around 7 Å and can pass the trimethylamine molecules. For example, in case of the 8-membered ring SAPO of chabazite structure, when a SAPO whose ratio of peak intensity at (100) plane of AFI structure to peak intensity at (100) plane of chabazite structure exceeds 0.02 is used for reaction, trimethylamine is more produced, thereby decreasing dimethylamine selectivity. For this reason, the present 8-membered ring SAPO of chabazite structure preferably has a ratio of peak intensity at (100) plane of AFI structure to peak intensity at (100) plane of chabazite structure in a range of 0.02 or less.

The 8-membered ring SAPO produced by the method of the present invention has a high purity and degree of crystallinity, and has an amorphous oxide layer of controlled thickness or surface composition in the preferable ranges described earlier. As a result, it exhibits excellent catalytic activity and dimethylamine selectivity in the production of methylamines by the reaction of methanol and ammonia, reaction of methanol and monomethylamine, and disproportionation reaction of monomethylamine.

In the present invention, the method for controlling temperature of hydrothermal treatment comprises the first step of carrying out hydrothermal treatment at 80 to 130° C. for 1 hour or more followed by hydrothermal treatment at 150 to 200° C. for 1 to 10 hours, and the second step of carrying out hydrothermal treatment at 150 to 200° C. for 10 hours or more.

In particular, it is a preferable condition of the temperature controlling method for hydrothermal treatment that hydrothermal treatment is carried out at a constant temperature in a range from 95 to 125° C. for 3 to 24 hours during the first step, and subsequent hydrothermal treatment is carried out at 150 to 200° C. for 10 to 150 hours as part of crystallization step of the first step and hydrothermal treatment of the second step since it stably provides crystalline silicoaluminophosphate molecular sieves which have 8-oxygen-membered ring micropores of chabazite structure and are pure and high in crystallinity.

Catalysts excellent in activity and dimethylamine selectivity can be stably produced when hydrothermal treatment is carried out at 80 to 130° C. for 1 hour or more followed by subsequent hydrothermal treatment at 150 to 200° C. during the first step. However, if the former hydrothermal treatment is, for example, carried out at above 130° C. for 1 hour or more, an AFI structure, which is not of an 8-membered ring SAPO, is notably formed, thereby decreasing dimethylamine selectivity. On the other hand, if it is carried out at below 80° C. for 1 hour or more, crystalline silicoaluminophosphate molecular sieves that have 8-oxygen-membered ring micropores are, as a whole, decreased in silicon content, thereby lowering catalytic activity.

Preferable heating patterns for the hydrothermal treatment carried out at 80 to 130° C. during the first step by elevating the temperature include heating from room temperature to 170° C. at a constant rate in 6 hours; heating from room temperature to 80° C. in 1 hour and from 80 to 170° C. at a constant rate in 3 hours; and heating from room temperature to 110° C. in 2 hours, keeping the temperature at 110° C. for 5 hours, and then heating up to 170° C.

On the other hand, it is not preferable to heat from 80 to 130° C. at a rate of 70° C./hour or more, because the AFI structure is notably produced. Also, it is not preferable to heat to 80° C. at a rate of 100° C./hour or more, because the starting mixture is often solidified. Meanwhile, there is no limitation to the condition of heating carried out between the hydrothermal treatment at 80 to 130° C. and the hydrothermal treatment at 150 to 200° C. in the first step.

Preferable time for the hydrothermal treatment at 150 to 200° C. during the second step varies depending upon hydrothermal treatment temperature and silicon content of the starting mixture, but is acceptable when it is 10 hours or more for which formation of the amorphous oxide layer sufficiently proceeds. It is preferably 10 to 150 hours for which the amorphous oxide layer of adequate thickness or surface composition can be stably formed on the crystal grain surface, and is more preferably 20 to 120 hours because an 8-membered ring SAPO having an amorphous oxide layer of thickness or surface composition sufficient for excellent catalytic activity and dimethylamine selectivity can be stably produced.

The hydrothermal treatment is carried out preferably with stirring rather than being allowed to stand, and more preferably, in such a manner that the mixture to be hydrothermally treated is sufficiently mixed uniformly.

The silicon compound useful as a starting material for production of the 8-membered ring SAPO of the present invention includes powdered silica, silica sol, orthosilicate, tetraethoxysilane and the like, of which silica sol is particularly preferable. Amount of the silica compound to be used is not limited, but preferably it is used in a $SiO_2/Al_2O_3$ molar ratio of 0.1 to 0.6, assuming that the starting mixture is represented by the ratio of oxides. The aluminum compound useful as the starting material includes pseudoboehmite, boehmite, gibbsite, bayerite, aluminum oxide such as γ-alumina, aluminum hydroxide, hydrated aluminum oxide, aluminum alkoxide such as aluminum triisopropoxide, and the like, of which pseudoboehmite is particularly preferable in consideration of material cost, availability and reactivity. On the other hand, aluminates, e.g., sodium aluminate, are not desirable because they normally need not only a usually-required calcination step but also ion exchange of cation, e.g., sodium ion, thereby requiring troublesome post-treatment.

The particularly preferable phosphorus compound useful as the starting material is orthophosphoric acid, although not limited thereto. Amount of phosphoric acid to be used is not limited, but preferably it is incorporated in a $P_2O_5/Al_2O_3$ molar ratio of 0.7 to 1.1, assuming that the starting mixture is represented by the ratio of oxides. Aluminum phosphate may be used in replace of the aluminum compound and the phosphorus compound, or in combination with the aluminum compound or the phosphorus compound. Amount of water to be used is not limited, so long as it gives a slurry having a concentration that allows it to be stirred uniformly. However, it is preferably used in a water/$Al_2O_3$ molar ratio of 100 or less in consideration of industrial productivity.

The organic amine and organic ammonium salt used as the structure directing agent include primary, secondary and tertiary amines, quaternary ammonium salts, aminoalcohols and diamines. The organic amine and organic ammonium salt with which an 8-membered ring SAPO is easily synthesized include tetraethyl ammonium hydroxide, triethylmethyl ammonium hydroxide, diethanolamine, diethylethanolamine, morpholine, methylbutylamine, diisopropylamine, di-n-propylamine, quinuclidine, cyclohexylamine, and N,N,N',N'-tetramethyl-1,6-hexanediamine. These organic amines and organic ammonium salts may be used either singly or as a mixture of two or more of them. An alkyl ammonium hydroxide may contain a chloride or bromide originating from its raw material. These impurities, however, are not considered to cause serious problems. Of these structure directing agents, tetraethyl ammonium hydroxide is more preferable for production of an 8-membered ring SAPO of chabazite structure, considering its average grain diameter and shape.

Amount of the organic amine and/or organic ammonium salt to be used for synthesizing an 8-membered ring SAPO is not limited. However, an 8-membered ring SAPO of high purity and crystallinity can be produced even when a ratio of the total mole number of the organic amine and organic ammonium salt to the mole number of the aluminum compound as $Al_2O_3$ is within a range of 0.4 to 0.98, and hence this range of ratio is preferable. For synthesis of an 8-membered ring SAPO of chabazite structure, the ratio of the total mole number of the organic amine and organic ammonium salt to the mole number of the aluminum compound as $Al_2O_3$ is preferably 0.4 to 0.98 since SAPOs of high purity and crystallinity can be produced. Even when the molar ratio of the total of the organic amine and organic ammonium salt to $Al_2O_3$ exceeds 0.98, an 8-membered ring SAPO of chabazite structure can be produced, but undesirably shaped grains, namely, plate grains are produced, or the use of excessive amines or ammonium salts causes increase in cost of raw materials or decrease in catalyst yield. Also, these surplus amines and ammonium salts are discharged as a waste liquid in separation/washing step after the hydrothermal treatment, and are not desirable considering additional cost for disposal and environmental load. When the molar ratio of the total of the organic amine and organic ammonium salt is below 0.40, a structure falling under an aluminum phosphate of JCPDS card No. 20-0045 is formed, thereby decreasing catalytic activity and dimethylamine selectivity.

In general, the 8-membered ring SAPO has a shape of cube, rectangular parallelepiped, plate, rod, needle, sphere or a combination thereof. Of these shapes, preferable ones for the present 8-membered ring SAPO of chabazite structure are cube and rectangular parallelepiped having an average crystal grain diameter of 5 μm or less, particularly preferably cube and rectangular parallelepiped having an average crystal grain diameter of 1 to 4 μm. On the other hand, the plate shape having an average crystal grain diameter of 1 μm or less, and aggregates of plate-shaped grains are not desirable, because the 8-membered ring SAPO of chabazite structure having an average crystal grain diameter of 5 μm or less and cubic or rectangular parallelepiped shape exhibits excellent catalytic activity, dimethylamine selectivity and catalyst life in production of methylamines by the reaction of methanol and ammonia. The average grain diameter can be easily determined by laser-aided diffraction type particle size distribution analyzer, and grain shape can be determined by scanning electron microscopy.

The 8-membered ring SAPO synthesized under hydrothermal treatment conditions is subjected to filtration, decantation or centrifugal separation, and washing. Then, it is dried at 80 to 150° C., and calcined. The calcination is normally carried out in a flow of air or air/nitrogen mixture at 400 to 1000° C., particularly preferably 500 to 900° C.

The 8-membered ring SAPO of the present invention is used as a catalyst for reaction of methanol and ammonia, reaction of methanol and monomethylamine, or disproportionation reaction of monomethylamine, as it is or after it is molded by compression, tableting or extrusion molding. It is also applicable to other catalytic reactions, e.g., for production of lower olefins from methanol (MTO reaction).

When the 8-membered ring SAPO of the present invention is used as a catalyst to produce methylamines by the reaction of methanol and ammonia, the reaction of methanol and monomethylamine, or the disproportionation reaction of monomethylamine, these reactions may be carried out in a fixed or fluidized bed. Reaction temperature is preferably in a range from 200 to 400° C., particularly preferably 250 to 350° C. Reaction pressure is not limited, but normally preferably in a range from 0.1 to 10 MPa.

Hereinafter, the present invention is described by way of Examples and Comparative Examples which by no means limit the present invention. The drawings are explained below.

EXAMPLES

Figure 1:
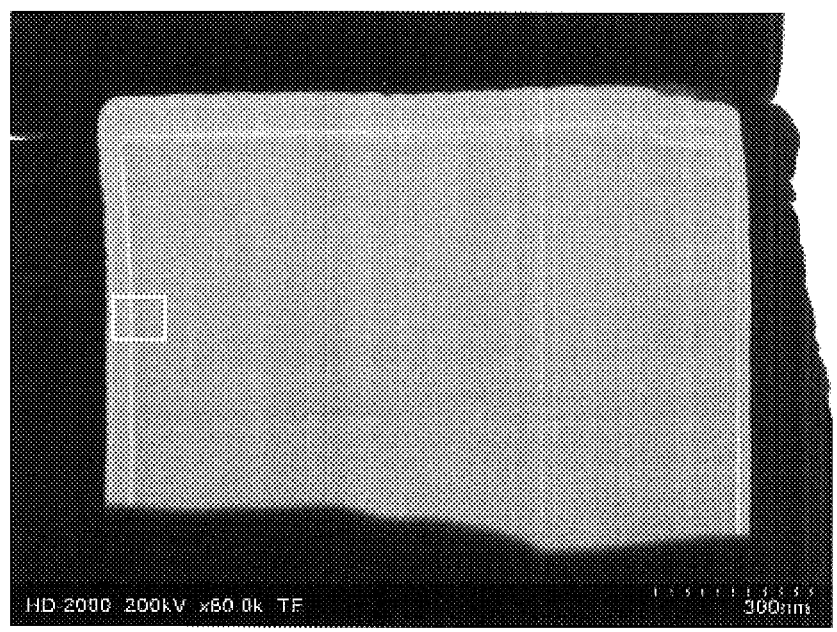
FIG. 1 shows a scanning transmission electron microscopic image (magnification: 80,000) of the catalyst prepared in Example 14.
Figure 2:
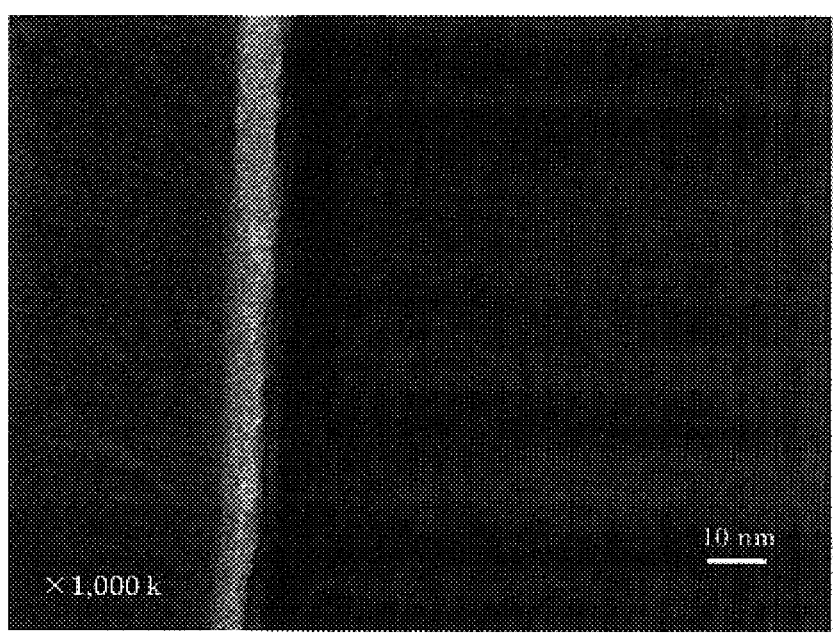
FIG. 2 shows a magnified image (magnification: 1,000,000) of the portion enclosed by the white frame appearing on the left side of FIG. 1.
Figure 3:
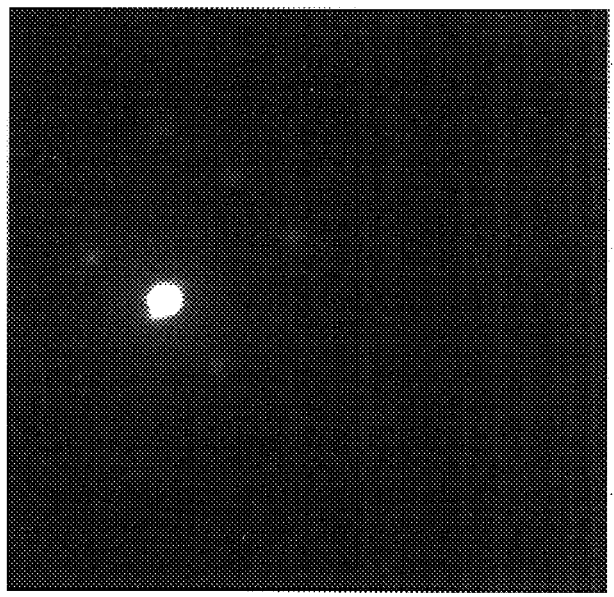
FIG. 3 shows an electron beam diffraction image of the portion with check pattern of FIG. 2.
Figure 4:
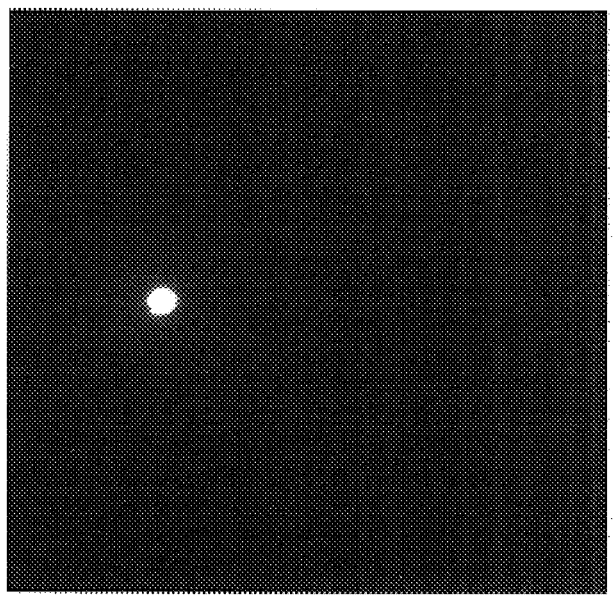
FIG. 4 shows an electron beam diffraction image of the white layer free of check pattern of FIG. 2.

Methods for measurement of physical and chemical properties, and synthesis procedures for methylamines, employed in the Examples, are described below. (1) Catalyst yield was expressed in weight percent by converting the weight each of silica, aluminum, phosphorus, titanium and zirconium compounds in the starting material charged in the autoclave into respective weights of $SiO_2$, $Al_2O_3$, $P_2O_5$, $TiO_2$ and $ZrO_2$, dividing the weight of the synthesized and calcined solid product by the total of the above converted weights, and then multiplying the quotient by 100. The weight of the synthesized solid product was measured as it was sufficiently dried (calcined powder) by drying at 110° C. for 8 hours after calcination.

(2) Purity of the 8-membered ring SAPO of chabazite structure in the synthesized solid product was determined by subjecting the calcined powder to X-ray diffractometry, and expressed as abundance ratio of AFI structure. The abundance ratio of AFI structure was obtained by dividing X-ray diffraction peak intensity at (100) plane of AFI structure by X-ray diffraction peak intensity at (100) plane of chabazite structure.

(3) Degree of crystallization was determined by subjecting calcined powders to X-ray diffractometry, and obtaining a ratio of peak intensity at (100) plane of chabazite structure of each of the calcined powders to peak intensity at (100) plane of the chabazite structure that was synthesized in Comparative Example 8 following the procedure described in the Catalyst Preparation Example 1 of Japanese Patent Laid-Open No. 2000-117114A.

(4) Shape of grain was determined by scanning transmission electron microscopic analysis (FE-SEM analysis).

(5) Average grain diameter was determined by a laser diffraction particle size analyzer.

(6) X-ray photoelectron spectroscopic analysis was carried out for calcined powders, so that surface composition was obtained based on the narrow spectral peak areas of the Si(2p), Al(2p) and P(2p) bands, corrected by Scofield correction factors.

(7) Reaction tests were carried out using catalysts prepared from the calcined powder which was tableted or compressed and granulated into the grains of 1 to 2 mm in size, in a flow type reactor system equipped with a feed tank, feed supply pump, inert gas charging unit, reactor tube (inner diameter: 13 mm, length: 300 mm, SUS 316), cooler, sampling tank, back pressure valve, and so on.

(8) Composition of reaction products was analyzed by gas chromatography for a sample collected for 30 minutes.

1. Synthesis of 8-Membered Ring SAPO (Relationship with Amount of Structure Directing Agent and Conditions of Hydrothermal Treatment)

Examples 1 to 9 and Comparative Examples 1 to 9 show synthesis examples of 8-membered ring SAPOs, in which the amount of tetraethyl ammonium hydroxide as a structure directing agent and the heating condition of hydrothermal treatment were varied. Table 1 summarizes catalyst yield, abundance ratio of AFI structure, degree of crystallization, and grain shape and size observed in the Examples and the Comparative Examples. Table 2 summarizes the reaction test results. The reaction test was carried out using a reactor tube charged with 2.5 g (3.5 mL) of granulated catalysts, feeding thereto a methanol/ammonia mixture (1:1 by weight) at a rate of 8.62 g/hour and a space velocity (GHSV) of 2500 $hour^{-1}$, and conducting reaction at a temperature of 305° C. and a pressure of 2 MPa.

Example 1

A uniform mixture of 85% by weight phosphoric acid (46.12 g) and pure water (191.16 g) was cooled to 30° C. or lower, to which pseudoboehmite (26.32 g: PURAL SB from SASOL GERMANY GmbH, $Al_2O_3$ content: 77.5%) was added with stirring. The resulting mixture was stirred for 30 minutes, and then 35% by weight aqueous solution of tetraethyl ammonium hydroxide (79.94 g) was added thereto while it was cooled to 30° C. or lower under stirring. The resulting mixture was stirred for 1 hour, and then silica sol (18.04 g: SNOWTEX N from Nissan Chemical Industries Ltd., $SiO_2$ content: 20% by weight) was added thereto, and further stirred for 30 minutes. The resulting mixture had a composition in terms of oxide molar ratio as follows: 0.95 TEAOH:1.0 $Al_2O_3$:1.0 $P_2O_5$:0.3 $SiO_2$:75 $H_2O$ (TEAOH: tetraethyl ammonium hydroxide). The resulting mixture was hydrothermally treated with stirring at 400 rpm in a stainless steel autoclave of 0.6 L in inner volume. In the hydrothermal treatment, temperature as of the contents was elevated at 25° C./hour from 25 to 170° C. in the first step, and kept at 170° C. for 35 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 600° C. for 4 hours, to obtain white powder (40.35 g). Catalyst yield was 77%. The product powder was a pure 8-membered ring SAPO of chabazite structure, as confirmed by X-ray diffractometry, which detected no peak for AFI structure or the compound of JCPDS card No. 20-0045. It had a high degree of crystallization of 1.00, and was composed of crystal grains which were cubic and highly uniform both in size and shape. It had an average grain diameter of 1.8 μm. It exhibited reaction performance 6 hours after the beginning of feed of raw materials as follows: 92 wt % in methanol conversion, 39 wt % in monomethylamine selectivity, 54 wt % in dimethylamine selectivity and 7 wt % in trimethylamine selectivity, as shown in Table 2.

Example 2

A white calcined powder (40.50 g) was prepared in the same manner as in Example 1, except that temperature as of the contents under hydrothermal treatment was elevated at 73° C./hour from 25 to 115° C., kept at 115° C. for 5 hours, and then elevated at 73° C./hour from 115 to 170° C. in the first step, and then kept at 170° C. for 35 hours in part of crystallization step of the first step and in the second step. Table 1 shows catalyst yield, abundance ratio of AFI structure, degree of crystallization, grain shape and average grain diameter. Table 2 shows reaction performance 6 hours after the beginning of feed of raw materials.

Example 3

A white calcined powder (46.15 g) was prepared in the same manner as in Example 2, except that the addition amount of 35% by weight aqueous solution of tetraethyl ammonium hydroxide was changed to 63.14 g, and the addition amount of pure water was changed to 202.07 g. The hydrothermally treated mixture had a composition in terms of oxide molar ratio as follows: 0.75 TEAOH:1.0 $Al_2O_3$:1.0 $P_2O_5$:0.3 $SiO_2$:75 $H_2O$. Table 1 shows catalyst yield, abundance ratio of AFI structure, degree of crystallization, grain shape and average grain diameter. Table 2 shows reaction performance 6 hours after the beginning of feed of raw materials.

Example 4

A white calcined powder (46.05 g) was prepared in the same manner as in Example 3, except that temperature as of the contents under hydrothermal treatment was elevated at 73° C./hour from 25 to 80° C., at 50° C./hour from 80 to 130° C. and at 70° C./hour from 130 to 170° C. in the first step, and kept at 170° C. for 35 hours in part of crystallization step of the first step and in the second step. Table 1 shows catalyst yield, abundance ratio of AFI structure, degree of crystallization, grain shape and average grain diameter. Table 2 shows reaction performance 6 hours after the beginning of feed of raw materials.

Example 5

A white calcined powder (45.94 g, catalyst yield: 88%) was prepared in the same manner as in Example 2, except that the addition amount of 35% by weight aqueous solution of tetraethyl ammonium hydroxide was changed to 42.10 g, and the addition amount of pure water was changed to 215.74 g. The hydrothermally treated mixture had a composition in terms of oxide molar ratio as follows: 0.50 TEAOH:1.0 $Al_2O_3$:1.0 $P_2O_5$:0.3 $SiO_2$:75 $H_2O$. The resulting calcined powder was subjected to X-ray diffractometry which detected a small peak of the compound of JCPDS card No. 20-0045, in addition to the peak of chabazite structure, but no peak of AFI structure observed in the catalyst prepared in Comparative Example 3 at the same TEAOH/ $Al_2O_3$ molar ratio. The powder had a degree of crystallization of 0.65 which was higher than Comparative Example 3. Shape of crystal grains was cubic, and average grain diameter was 1.1 μm. This example indicates that an 8-membered ring SAPO of chabazite structure having higher purity and degree of crystallization can be obtained even at the same TEAOH/$Al_2O_3$ molar ratio of 0.50 as Comparative Example 3 by keeping the temperature at 115° C. for 5 hours when hydrothermal treatment is carried out in the first step.

Example 6

A uniform starting mixture of 85% by weight phosphoric acid (46.12 g), pure water (108.99 g) and 35% by weight aqueous solution of tetraethyl ammonium hydroxide (63.14 g) was cooled to 30° C. or lower, to which pseudoboehmite (26.32 g: PURAL NF from SASOL GERMANY GmbH, $Al_2O_3$ content: 77.5%) was added with stirring. The resulting mixture was stirred for 1 hour, and then silica sol (18.04 g: SNOWTEX N from Nissan Chemical Industries Ltd., $SiO_2$ content: 20% by weight) and titania sol (4.04 g: STS-01 from Ishihara Sangyo Kaisha, Ltd., $TiO_2$ content: 29.5% by weight) were added thereto, and further stirred for 30 minutes. The resulting mixture had a composition in terms of oxide molar ratio as follows: 0.75 TEAOH:1.0 $Al_2O_3$:1.0 $P_2O_5$:0.3 $SiO_2$:0.075 $TiO_2$:50 $H_2O$. The resultant starting mixture was hydrothermally treated with stirring at 500 rpm in a stainless steel autoclave of 0.6 L in inner volume. In the hydrothermal treatment, temperature as of the contents was elevated at 65° C./hour from 25 to 110° C., kept at 110° C. for 5 hours, and then elevated at 65° C./hour from 110 to 160° C. in the first step, and kept at 160° C. for 35 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 800° C. for 4 hours, to obtain white powder (48.30 g). Catalyst yield was 90%. The product powder was a pure 8-membered ring SAPO of chabazite structure, as confirmed by X-ray diffractometry, which detected no peak of AFI structure or the compound of JCPDS card No. 20-0045. It had a high degree of crystallization of 1.10, and was composed of crystal grains which were cubic and highly uniform both in size and shape. It had an average grain diameter of 1.7 μm.

It exhibited reaction performance 6 hours after the beginning of feed of raw materials as follows: 94 wt % in methanol conversion: 37 wt % in monomethylamine selectivity, 60 wt % in dimethylamine selectivity and 3 wt % in trimethylamine selectivity, as shown in Table 2.

Example 7

A white calcined powder (47.81 g) was prepared in the same manner as in Example 6, except that temperature as of the contents under hydrothermal treatment was elevated at 65° C./hour from 25 to 125° C., kept at 125° C. for 24 hours, and then elevated at 65° C./hour from 125 to 170° C. in the first step, and kept at 170° C. for 35 hours in part of crystallization step of the first step and in the second step. Table 1 shows catalyst yield, abundance ratio of AFI structure, degree of crystallization, grain shape and average grain diameter. Table 2 shows reaction performance 6 hours after the beginning of feed of raw materials.

Example 8

A white calcined powder (47.09 g) was prepared in the same manner as in Example 6, except that temperature as of the contents under hydrothermal treatment was elevated at 65° C./hour from 25 to 90° C., kept at 90° C. for 5 hours and then elevated at 65° C./hour from 90 to 165° C. in the first step, and kept at 165° C. for 12 hours in part of crystallization step of the first step and in the second step. Table 1 shows catalyst yield, abundance ratio of AFI structure, degree of crystallization, grain shape and average grain diameter. Table 2 shows reaction performance 6 hours after the beginning of feed of raw materials.

Example 9

A white calcined powder (50.43 g, catalyst yield: 92%) was prepared in the same manner as in Example 6, except that the addition amount of 35% by weight aqueous solution of tetraethyl ammonium hydroxide was changed to 42.09 g, the addition amount of pure water was changed to 118.0 g, and the addition amount of silica sol was changed to 24.05 g, and temperature as of the content under hydrothermal treatment was elevated at 20° C./hour from 25 to 115° C., kept at 115° C. for 5 hours and then elevated at 20° C./hour from 115 to 170° C. in the first step, and kept at 170° C. for 50 hours in part of crystallization step of the first step and in the second step. The hydrothermally treated mixture had a composition in terms of oxide molar ratio as follows: 0.50 TEAOH:1.0 $Al_2O_3$:1.0 $P_2O_5$:0.4 $SiO_2$:0.075 $TiO_2$:50 $H_2O$. Table 1 shows catalyst yield, abundance ratio of AFI structure, degree of crystallization, grain shape and average grain diameter. Table 2 shows reaction performance 6 hours after the beginning of feed of raw materials.

Comparative Example 1

A white calcined powder (40.32 g) was prepared in the same manner as in Example 1, except that temperature as of the contents under hydrothermal treatment was elevated at 79° C./hour from 25 to 170° C. in the first step, and kept at 170° C. for 42 hours in part of crystallization step of the first step and in the second step. The product powder was subjected to X-ray diffractometry which detected the peak of AFI structure which is not of an 8-memberded ring SAPO, in addition to the peak of chabazite structure which is of an 8-membered ring SAPO. It had an abundance ratio of AFI structure of 0.03. No peak for the compound of JCPDS card No. 20-0045 was detected. However, it had a low degree of crystallization of 0.89. Shape of crystal grains was cubic, but there were found some hexagonal columnar crystals which are considered to be of AFI structure. They had an average grain diameter of 1.8 μm. Table 2 shows reaction performance 6 hours after the beginning of feed of raw materials.

Comparative Example 2

A white calcined powder (43.30 g) was prepared in the same manner as in Example 3, except that temperature as of the contents under hydrothermal treatment was elevated at 78° C./hour from 25 to 170° C. in the first step, and kept at 170° C. for 35 hours in part of crystallization step of the first step and in the second step. The product powder was subjected to X-ray diffractometry, which detected the peak of AFI structure which is not of an 8-membered ring SAPO, and the peak of the compound of JCPDS card No. 20-0045, in addition to the peak of chabazite structure which is of an 8-membered ring SAPO. It had an abundance ratio of AFI structure of 0.03 and a low degree of crystallization of 0.79. Shape of crystal grains was rectangular parallelepiped, but there were found some hexagonal columnar crystals which are considered to be of AFI structure and some amorphous grains which are considered to be of an amorphous compound. They had an average grain diameter of 1.5 μm. Table 2 shows reaction performance 6 hours after the beginning of feed of raw materials.

Comparative Example 3

A white calcined powder (43.40 g) was prepared in the same manner as in Example 5, except that temperature as of the contents under hydrothermal treatment was elevated at 78° C./hour from 25 to 170° C. in the first step, and kept at 170° C. for 35 hours in part of crystallization step of the first step and in the second step. The product powder was subjected to X-ray diffractometry, which detected the peak of AFI structure which is not of an 8-membered ring SAPO, and the peak of the compound of JCPDS card No. 20-0045, in addition to the peak of chabazite structure which is of an 8-membered ring SAPO. It had an abundance ratio of AFI structure of 0.10 and a low degree of crystallization of 0.32.

Comparative Example 4

A white calcined powder (45.51 g) was prepared in the same manner as in Example 2, except that the addition amount of 35% by weight aqueous solution of tetraethyl ammonium hydroxide was changed to 21.05 g, and the addition amount of pure water was changed to 229.43 g. The hydrothermally treated mixture had a composition in terms of oxide molar ratio as follows: 0.25 TEAOH:1.0 $Al_2O_3$:1.0 $P_2O_5$:0.3 $SiO_2$:75 $H_2O$. The product calcined powder was subjected to X-ray diffractometry, which confirmed it to be the compound of JCPDS card No. 20-0045, and detected no peak of chabazite or AFI structure.

Comparative Example 5

A white calcined powder (47.65 g) was prepared in the same manner as in Example 6, except that temperature as of the contents under hydrothermal treatment was elevated at 65° C./hour from 25 to 135° C., kept at 135° C. for 5 hours and then elevated at 65° C./hour from 135 to 170° C. in the first step, and kept at 170° C. for 35 hours in part of crystallization step of the first step and in the second step. The product powder was subjected to X-ray diffractometry, which detected the peak of AFI structure, in addition to the peak of chabazite structure, but no peak of the compound of JCPDS card No. 20-0045. It had an abundance ratio of AFI structure of 0.04 and a degree of crystallization of 0.98. Shape of crystal grains was cubic, and there were also found some needle-shaped crystals which are considered to be of AFI structure. They had an average grain diameter of 1.9 μm. Table 2 shows reaction performance 6 hours after the beginning of feed of raw materials.

Comparative Example 6

A white calcined powder (45.65 g) was prepared in the same manner as in Example 6, except that temperature as of the contents under hydrothermal treatment was elevated at 65° C./hour from 25 to 70° C., kept at 70° C. for 5 hours and then elevated at 65° C./hour from 70 to 170° C. in the first step, and kept at 170° C. for 35 hours in part of crystallization step of the first step and in the second step. The product powder was subjected to X-ray diffractometry, which detected the peak of AFI structure, in addition to the peak of chabazite structure which is of an 8-membered ring SAPO, but no peak of the compound of JCPDS card No. 20-0045. It had an abundance ratio of AFI structure of 0.03 and a degree of crystallization of 0.90. Shape of crystal grains was thick plate. They had an average grain diameter of 1.5 μm. Table 2 shows reaction performance 6 hours after the beginning of feed of raw materials.

Comparative Example 7

A white calcined powder (36.40 g, catalyst yield: 66%) was prepared in the same manner as in Example 9, except that the addition amount of 35% by weight aqueous solution of tetraethyl ammonium hydroxide was changed to 105.23 g, and the addition amount of pure water was changed to 76.93 g, and the hydrothermal treatment was carried out while stirring was made at 200 rpm. The hydrothermally treated mixture had a composition in terms of oxide molar ratio as follows: 1.25 TEAOH:1.0 $Al_2O_3$:1.0 $P_2O_5$:0.4 $SiO_2$:0.075 $TiO_2$:50 $H_2O$. The product calcined powder was subjected to X-ray diffractometry, which confirmed it to be of pure chabazite structure, but detected no peak of AFI structure or the compound of JCPDS card No. 20-0045. It had a low degree of crystallization of 0.65. Shape of crystal grains was thin plate. They had an average grain diameter of 0.6 μm. Table 2 shows reaction performance 6 hours after the beginning of feed of raw materials.

Comparative Example 8

Zirconia-modified SAPO-34 was prepared in the same manner as in the Catalyst Preparation Example 1 described in Japanese Patent Laid-Open No. 2000-117114A. A uniform mixture of 35% by weight aqueous solution of tetraethyl ammonium hydroxide (151.41 g) and pure water (84.60 g) was cooled to 5° C., to which aluminum isopropoxide (81.80 g: from Nacalai Tesque, Inc.) was added, and the mixture was stirred at a high speed for 15 minutes. Then, silica sol (18.04 g) and powdered zirconium oxide (2.40 g: RC-100 from Daiichi Kigenso Kagaku Kogyo Co., Ltd.) were added thereto, and the mixture was stirred at a high speed for 15 minutes until it became uniform. The resulting mixture was then supplemented with 85% by weight phosphoric acid (46.20 g), stirred in a similar manner for 5 minutes, and then ground for 1 hour. The resulting mixture had a composition in terms of oxide molar ratio as follows: 1.80 TEAOH:1.0 $Al_2O_3$:1.0 $P_2O_5$:0.3 $SiO_2$:0.097 $ZrO_2$:57 $H_2O$. The resulting mixture was hydrothermally treated with stirring at 200 rpm in a stainless steel autoclave of 0.6 L in inner volume. In the hydrothermal treatment, temperature as of the contents was elevated at 75° C./hour from 25 to 200° C., and kept at 200° C. for 4 hours, where hydrothermal treatment pressure was self-generated. The autoclave was cooled to room temperature and opened. The product slurry was centrifugally separated to obtain the precipitate, which was washed and centrifugally separated using 200 mL of pure water 4 times, and then dried at 80° C. for 12 hours. It was then calcined under air flow at 600° C. for 4 hours, to obtain white powder (34.21 g). Catalyst yield was 62%. The product powder was subjected to X-ray diffractometry, which confirmed it to be of pure chabazite structure, and detected no peak of AFI structure or the compound of JCPDS card No. 20-0045. Shape of crystal grains was cubic, and they were uniform both in size and shape. They had an average grain diameter of 1.4 μm. It exhibited reaction performance 6 hours after the beginning of feed of raw materials as follows: 90 wt % in methanol conversion, 41 wt% in monomethylamine selectivity, 54 wt % in dimethylamine selectivity, and 5 wt % in trimethylamine selectivity, as shown in Table 2.

Comparative Example 9

A zirconia-modified SAPO-34 was prepared in the same manner as in Comparative Example 8, to yield white calcined powder (32.55 g, catalyst yield: 59%). This powder was subjected to X-ray diffractometry, which confirmed it to be of pure chabazite structure, and detected no peak of AFI structure or the compound of JCPDS card No. 20-0045. Shape of crystal grains was cubic, and they were highly uniform both in size and shape. They had an average grain diameter of 1.6 μm. Table 2 shows reaction performance 6 hours after the beginning of feed of raw materials.

TABLE 1

| Examples | TEAOH/ $Al_2O_3$ molar ratio | $H_2O$/ $Al_2O_3$ molar ratio | Heating rate in hydrothermal treatment (° C./h) | Temperature and time for which the temperature is kept during the first step | Temperature and time for which the temperature is kept during the second step*1) | Catalyst yield (%) | Abundance ratio of AFI structure | Degree of crystallization | Grain shape | Grain diameter (μm) |
|---|---|---|---|---|---|---|---|---|---|---|
| Ex. 1 | 0.95 | 75 | 25 | — | 170° C., 35 h | 77 | 0 | 1.00 | Cubic | 1.8 |
| Ex. 2 | 0.95 | 75 | 73 | 115° C., 5 h | 170° C., 35 h | 77 | 0 | 1.00 | Cubic | 1.7 |
| Ex. 3 | 0.75 | 75 | 73 | 115° C., 5 h | 170° C., 35 h | 88 | 0 | 1.15 | Rectangular parallelepiped | 1.7 |
| Ex. 4 | 0.75 | 75 | 73 | *2 | 170° C., 35 h | 88 | 0 | 1.04 | Cubic | 1.5 |
| Ex. 5 | 0.50 | 75 | 73 | 115° C., 5 h | 170° C., 35 h | 88 | 0 | 0.65 | Cubic | 1.1 |
| Ex. 6 | 0.75 | 50 | 65 | 110° C., 5 h | 160° C., 35 h | 90 | 0 | 1.10 | Cubic | 1.7 |
| Ex. 7 | 0.75 | 50 | 65 | 125° C., 24 h | 170° C., 35 h | 89 | 0 | 1.09 | Cubic | 1.7 |
| Ex. 8 | 0.75 | 50 | 65 | 90° C., 5 h | 165° C., 12 h | 88 | 0 | 1.04 | Rectangular parallelepiped | 1.6 |
| Ex. 9 | 0.50 | 50 | 20 | 115° C., 5 h | 170° C., 50 h | 92 | 0 | 1.05 | Cubic | 1.8 |
| C. Ex. 1 | 0.95 | 75 | 79 | — | 170° C., 42 h | 77 | 0.03 | 0.89 | Cubic | 1.8 |
| C. Ex. 2 | 0.75 | 75 | 78 | — | 170° C., 35 h | 83 | 0.03 | 0.79 | Rectangular parallelepiped | 1.5 |
| C. Ex. 3 | 0.50 | 75 | 78 | — | 170° C., 35 h | 83 | 0.10 | 0.32 | — | — |
| C. Ex. 4 | 0.25 | 75 | 73 | 115° C., 5 h | 170° C., 35 h | 87 | — | *3 | — | — |
| C. Ex. 5 | 0.75 | 50 | 65 | 135° C., 5 h | 170° C., 35 h | 89 | 0.04 | 0.98 | Cubic + Needle | 1.9 |
| C. Ex. 6 | 0.75 | 50 | 65 | 70° C., 5 h | 170° C., 35 h | 85 | 0.03 | 0.90 | Plate | 1.5 |
| C. Ex. 7 | 1.25 | 50 | 20 | 115° C., 5 h | 170° C., 50 h | 66 | 0 | 0.65 | Plate | 0.6 |

TABLE 1-continued

| Examples | TEAOH/ Al$_2$O$_3$ molar ratio | H$_2$O/ Al$_2$O$_3$ molar ratio | Heating rate in hydro- thermal treatment (° C./h) | Temperature and time for which the temperature is kept during the first step | Temperature and time for which the temperature is kept during the second step*1) | Cata- lyst yield (%) | Abundance ratio of AFI structure | Degree of crystalli- zation | Grain shape | Grain diameter (μm) |
|---|---|---|---|---|---|---|---|---|---|---|
| C. Ex. 8 | 1.80 | 57 | 75 | — | 200° C., 4 h | 62 | 0 | 1.00 | Cubic | 1.4 |
| C. Ex. 9 | 1.80 | 57 | 75 | — | 200° C., 4 h | 59 | 0 | 0.96 | Cubic | 1.6 |

*1)Part of crystallization step of the first step is included.
*2: Temperature was elevated at 50° C./hour from 80 to 130° C.
*3: An aluminum phosphate structure of JCPDS card No. 20-0045 was formed.
TEAOH/Al$_2$O$_3$ molar ratio: Ratio of mole number of TEAOH to mole number of aluminum compound as Al$_2$O$_3$
Abundance ratio of AFI structure = Peak intensity at (100) plane of AFI structure/peak intensity at (100) plane of chabazite structure.
Degree of crystallization = Peak intensity at (100) plane of chabazite structure prepared in each example/peak intensity at (100) plane of the chabazite structure of Comparative Example 1.
Aluminum compound: Pseudoboehmite for Examples 1 to 9 and Comparative Examples 1 to 7, and aluminum triisopropoxide for Comparative Examples 8 and 9.
Ex. means Example, and C. Ex. means Comparative Example..

TABLE 2

| Examples | Methanol conversion (wt %) | Monometh- ylamine selec- tivity (wt %) | Dimeth- ylamine selec- tivity (wt %) | Trimeth- ylamine selec- tivity (wt %) |
|---|---|---|---|---|
| Example 1 | 92 | 39 | 54 | 7 |
| Example 2 | 96 | 36 | 56 | 8 |
| Example 3 | 96 | 37 | 60 | 3 |
| Example 4 | 95 | 37 | 55 | 8 |
| Example 6 | 94 | 37 | 60 | 3 |
| Example 7 | 96 | 36 | 58 | 6 |
| Example 8 | 92 | 40 | 55 | 5 |
| Example 9 | 92 | 40 | 58 | 2 |
| Comparative Example 1 | 87 | 40 | 50 | 10 |
| Comparative Example 2 | 83 | 43 | 48 | 9 |
| Comparative Example 5 | 98 | 36 | 48 | 16 |
| Comparative Example 6 | 87 | 40 | 50 | 9 |
| Comparative Example 7 | 85 | 31 | 51 | 18 |
| Comparative Example 8 | 90 | 41 | 54 | 5 |
| Comparative Example 9 | 86 | 43 | 54 | 3 |

Reaction conditions: Temperature: 305° C., Pressure: 2 MPa, GHSV: 2500 h$^{-1}$

Comparative Examples 1 to 3, 5 and 6 each provided a catalyst that contained AFI structure which is not of the 8-membered ring SAPO, and had a low degree of crystallization, in which the addition amount of tetraethyl ammonium hydroxide was 1.0 or less times the mole number of aluminum compound as Al$_2$O$_3$, and the hydrothermal treatment in the first step was carried out at a temperature in a range of from 80 to 130° C. but for a time shorter than 1 hour. Also, the methanol conversion and dimethylamine selectivity were low when reaction was carried out using these catalysts. By contrast, Examples 1 to 9 each provided a catalyst that contained no AFI structure or the compound of JCPDS card No. 20-0045, and had a high degree of crystallization, in which the hydrothermal treatment in the first step was carried out at a temperature in a range from 80 to 130° C. for 1 hour or more. Moreover, methanol conversion and dimethylamine selectivity resulting from the reaction using these catalysts were better than the catalysts of Comparative Examples 1, 2, 5 and 6. It is particularly noted that the catalysts prepared in Examples 3 and 6 gave excellent methanol conversion and dimethylamine selectivity, where tetraethyl ammonium hydroxide as a structure directing agent was used in amount of 0.75 times the mole number of pseudoboehmite as Al$_2$O$_3$, and temperature was kept at 115 or 125° C. for 1 hour or more to carry out the hydrothermal treatment in the first step. Comparative Examples 7 to 9 are examples in which tetraethyl ammonium hydroxide was used in an amount of 1.0 or more times the mole number of aluminum compounds as Al$_2$O$_3$. From these examples, it has been found that when the TEAOH/Al$_2$O$_3$ molar ratio exceeds 0.98, a pure 8-membered ring SAPO of chabazite structure can be synthesized but at a low catalyst yield of 59 to 66% and low catalyst productivity. These examples showed lower methanol conversion and dimethylamine selectivity than the catalysts prepared in Examples 1 to 9. Particularly, the catalyst of Comparative Example 7, which was plate-shaped crystals, was inferior in performance. As apparent from these examples, it has been found that an 8-membered ring SAPO of chabazite structure excellent in purity, degree of crystallization and catalyst performance can be obtained by controlling temperature during hydrothermal treatment even when a structure directing agent is used in a small amount that has conventionally been considered impossible. Rather, it was shown that the low TEAOH/Al$_2$O$_3$ molar ratio of 0.75 gave superior degree of crystallization and catalyst performance. Particularly, Comparative Examples 8 and 9 was to investigate synthesis reproducibility of the Catalyst Preparation Example described in Japanese Patent Laid-Open No. 2000-117114A, and revealed that methanol conversion is not always reproduced, as in Comparative Example 9. Comparative Example 4 was an example in which synthesis was carried out using tetraethyl ammonium hydroxide in an amount of 0.25 times the mole number of pseudoboehmite as Al$_2$O$_3$, and yielded a solid product having a structure of JCPDS card No. 20-0045, but did not produce any 8-membered ring SAPO of chabazite structure. On the other hand, Example 9 in which tetraethyl ammonium hydroxide was used in an amount of 0.50 times the Al$_2$O$_3$ yielded a pure 8-membered ring SAPO of chabazite structure exhibiting good catalyst performance.

2. Examples Using Tetraethyl Ammonium Hydroxide and Diethanolamine, or Cyclohexylamine as Structure Directing Agents Examples 10 is an example for synthesis of an 8-membered ring SAPO of chabazite structure using a mixture of tetraethyl ammonium hydroxide and diethanolamine as structure directing agents, and Example 11 is the same except using cyclohexylamine as a structure directing agent. Table 3 shows results of the reaction tests using the synthesized catalysts. The reaction tests were carried out in the same manner as in Examples 1 to 9.

Example 10

A uniform mixture of 85% by weight phosphoric acid (41.51 g), pure water (98.70 g), 35% by weight aqueous solution of tetraethyl ammonium hydroxide (42.10 g) and diethanolamine (6.30 g) was cooled to 30° C. or lower, to which pseudoboehmite (26.32 g: PURAL NF from SASOL GERMANY GmbH, $Al_2O_3$ content: 77.5%) was added with stirring. The resulting mixture was stirred for 1 hour, and then silica sol (30.06 g: SNOWTEX N from Nissan Chemical Industries Ltd., $SiO_2$ content: 20% by weight) and powdered zirconium oxide (1.25 g: RC-100 from Daiichi Kigenso Kagaku Kogyo Co., Ltd.) were added thereto, and further stirred for 30 minutes. The resulting mixture had a composition in terms of oxide molar ratio as follows: 0.50 TEAOH:0.30 DEA:1.0 $Al_2O_3$:0.9 $P_2O_5$:0.5 $SiO_2$:0.05 $ZrO_2$: 45 $H_2O$ (DEA: diethanolamine). The resulting mixture was hydrothermally treated with stirring in a stainless steel autoclave. In the hydrothermal treatment, temperature as of the contents was elevated at 65° C./hour from 25 to 115° C., kept at 115° C. for 5 hours and then elevated at 65° C./hour from 115 to 170° C. in the first step, and kept at 170° C. for 35 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 600° C. for 4 hours, to obtain white powder (44.17 g). Catalyst yield was 85%. The product powder was a pure 8-membered ring SAPO of chabazite structure, as confirmed by X-ray diffractometry, which detected no peak of AFI structure or the compound of JCPDS card No. 20-0045. It had a high degree of crystallization of 1.03, and was composed of crystal grains which were rectangular parallelepiped and highly uniform both in size and shape. It had an average grain diameter of 2.5 μm. Table 3 shows reaction performance 6 hours after the beginning of feed of raw materials.

Example 11

A uniform mixture of 85% by weight phosphoric acid (43.82 g) and pure water (145.50 g) was cooled to 30° C. or lower, to which aluminum triisopropoxide (81.70 g: from Nacalai Tesque, Inc.) was added with stirring. The resulting mixture was stirred for 30 minutes, and then cyclohexylamine (15.90 g) was added thereto with stirring. The resulting mixture was stirred for 1 hour, and then silica sol (24.05 g: SNOWTEX N from Nissan Chemical Industries Ltd., $SiO_2$ content: 20% by weight) was added thereto, and further stirred for 30 minutes. The resulting mixture had a composition in terms of oxide molar ratio as follows: 0.80 cyclohexylamine:1.0 $Al_2O_3$:0.95 $P_2O_5$:0.40 $SiO_2$:47.5 $H_2O$. The resulting mixture was hydrothermally treated with stirring in a stainless steel autoclave. In the hydrothermal treatment, temperature as of the contents was elevated at 65° C./hour from 25 to 115° C., kept at 115° C. for 5 hours and then elevated at 65° C./hour from 115 to 180° C. in the first step, and kept at 180° C. for 35 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 600° C. for 4 hours, to obtain white powder (43.90 g). Catalyst yield was 84%. The product powder was a pure 8-membered ring SAPO of chabazite structure, as confirmed by X-ray diffractometry, which detected no peak of AFI structure or the compound of JCPDS card No. 20-0045. It had a high degree of crystallization of 1.00, and composed of crystal grains which were cubic and highly uniform both in size and shape. It had an average grain diameter of 3.5 μm. Table 3 shows reaction performance 6 hours after the beginning of feed of raw materials.

TABLE 3

| Examples | Structure directing agent | Structure directing agent/$Al_2O_3$ molar ratio | Heating rate in hydrothermal treatment (° C./h) | Temperature and time for which the temperature is kept during the first step | Temperature and time for which the temperature is kept during the second step*1) | Methanol conversion (wt %) | Monomethylamine selectivity (wt %) | Dimethylamine selectivity (wt %) | Trimethylamine selectivity (wt %) |
|---|---|---|---|---|---|---|---|---|---|
| Example 10 | TEAOH + DEA | 0.8 | 65 | 115° C. 5 h | 170° C. 35 h | 94 | 38 | 56 | 6 |
| Example 11 | Cyclohexylamine | 0.8 | 65 | 115° C. 5 h | 180° C. 35 h | 90 | 41 | 54 | 5 |

*1)Part of crystallization step in the first step is included.
Structure directing agent/$Al_2O_3$ molar ratio: Sum of molar ratio of organic amine and molar ratio of organic ammonium salt to aluminum compound as $Al_2O_3$.
DEA: Diethanolamine
Reaction conditions: Temperature: 305° C., Pressure: 2 MPa, GHSV: 2500 hour$^{-1}$ Both Examples produced pure 8-membered ring SAPOs of chabazite structure exhibiting good catalyst performance by use of structure directing agents in an amount of less than 1.0 times the mole number of aluminum compounds as $Al_2O_3$.

3. Relationship of Surface Composition and Thickness of Amorphous Oxide Layer with Catalyst Performance Examples 12 to 17 and Comparative Examples 10 and 11 deal with surface composition and thickness of the amorphous oxide layer and catalyst performance of the 8-membered ring SAPO of chabazite structure. Table 4 summarizes Si/Al atomic ratio of the whole crystal grain (bulk Si/Al atomic ratio), surface Si/Al atomic ratio, surface Si/P atomic ratio and amorphous oxide layer thickness of the catalyst prepared in each of the examples and comparative examples. Table 5 summarizes results of reaction tests. The reaction tests were carried out in the same manner as in Examples 1 to 9.

Example 12

The calcined powder prepared in Example 2 was analyzed by ICP and XPS. It had a Si/Al atomic ratio of the whole crystal grain of 0.15, surface Si/Al atomic ratio of 0.60 and surface Si/P atomic ratio of 0.66.

Example 13

The calcined powder prepared in Example 6 was analyzed by ICP and XPS. It had a Si/Al atomic ratio of the whole crystal grain of 0.14, surface Si/Al atomic ratio of 1.07 and surface Si/P atomic ratio of 1.24.

Example 14

A uniform mixture of 85% by weight phosphoric acid (89.8 g), pure water (183.9 g) and 35% by weight aqueous solution of tetraethyl ammonium hydroxide (122.9 g) was supplemented with pseudoboehmite (51.3 g: PURAL NF from SASOL GERMANY GmbH, $Al_2O_3$ content: 77.5%) with stirring. The resulting mixture was stirred for 1 hour, and then silica sol (46.8 g: SNOWTEX N from Nissan Chemical Industries Ltd., $SiO_2$ content: 20% by weight) and titania sol (5.3 g: STS-01 from Ishihara Sangyo Kaisha Ltd., $TiO_2$ content: 29.5% by weight) were added thereto, and further stirred for 30 minutes. The resulting mixture had a pH of 2.95, and had a composition in terms of oxide molar ratio as follows: 0.75 TEAOH:1.0 $Al_2O_3$:1.0 $P_2O_5$:0.4 $SiO_2$: 0.05 $TiO_2$:50 $H_2O$. The resulting mixture was hydrothermally treated with stirring at 700 rpm in a stainless steel autoclave of 0.6 L in inner volume. In the hydrothermal treatment, temperature as of the contents was elevated at 20° C./hour from 25 to 115° C., kept at 115° C. for 5 hours and then elevated at 20° C./hour from 115 to 170° C. in the first step, and kept at 170° C. for 50 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and dried at 80° C. for 12 hours. It was then calcined under air flow at 600° C. for 4 hours, to obtain white powder (88.2 g). Catalyst yield was 83% and good. The product powder was of pure chabazite structure, as confirmed by X-ray diffractometry, which detected no peak of AFI structure or the compound of JCPDS card No. 20-0045. It had a high degree of crystallization of 1.05, and composed of crystal grains which were cubic and highly uniform both in size and shape. It had an average grain diameter of 2.2 μm. The resultant calcined powder had a Si/Al atomic ratio of the whole crystal grain of 0.16, surface Si/Al atomic ratio of 1.61 and surface Si/P atomic ratio of 2.45. The crystal grains of the calcined powder had a 7 nm thick amorphous oxide layer, as observed by scanning transmission electron microscope. Table 5 shows reaction performance 6 hours after the beginning of feed of raw materials.

Example 15

A white calcined powder (86.2 g, catalyst yield: 81%) was prepared in the same manner as in Example 14, except that temperature as of the contents under hydrothermal treatment was elevated at 20° C./hour from 25 to 115° C., kept at 115° C. for 5 hours and then elevated at 20° C./hour from 115 to 170° C. in the first step, and kept at 170° C. for 100 hours in part of crystallization step of the first step and in the second step. The product powder was a pure 8-membered ring SAPO of chabazite structure, as confirmed by X-ray diffractometry, which detected no peak of AFI structure or the compound of JCPDS card No. 20-0045. It had a high degree of crystallization of 1.03, and composed of crystal grains which were cubic and highly uniform both in size and shape. It had an average grain diameter of 2.4 μm. The resultant calcined powder had a Si/Al atomic ratio of the whole crystal grain of 0.15, surface Si/Al atomic ratio of 1.98 and surface Si/P atomic ratio of 2.92. The crystal grains of the calcined powder had a 13 nm thick amorphous oxide layer, as observed by scanning transmission electron microscope. Table 5 shows reaction performance 6 hours after the beginning of feed of raw materials.

Example 16

A white calcined powder (45.70 g, catalyst yield: 87%) was prepared in the same manner as in Example 3, except that temperature as of the contents under hydrothermal treatment was elevated at 20° C./hour from 25 to 115° C., kept at 115° C. for 5 hours and then elevated at 20° C./hour from 115 to 170° C. in the first step, and kept at 170° C. for 30 hours in part of crystallization step of the first step and in the second step. The product powder was of pure chabazite structure, as confirmed by X-ray diffractometry, which detected no peak of AFI structure or the compound of JCPDS card No. 20-0045. It had a degree of crystallization of 1.00, and composed of crystal grains which were cubic and highly uniform both in size and shape. It had an average grain diameter of 1.9 μm. The resultant calcined powder had a Si/Al atomic ratio of the whole crystal grain of 0.14, surface Si/Al atomic ratio of 0.65 and surface Si/P atomic ratio of 0.75. Table 5 shows reaction performance 6 hours after the beginning of feed of raw materials.

Example 17

A white calcined powder (46.21 g, catalyst yield: 88%) was prepared in the same manner as in Example 16, except that temperature as of the contents under hydrothermal treatment was elevated at 20° C./hour from 25 to 115° C., kept at 115° C. for 5 hours, and then elevated at 20° C./hour from 115 to 170° C. in the first step, and kept at 170° C. for 20 hours in part of crystallization step of the first step and the second step, and the hydrothermally treated mixture was supplemented with silica sol (6.1 g: SNOWTEX N from Nissan Chemical Industries Ltd., $SiO_2$ content: 20% by weight) and further hydrothermally treated at 170° C. for 10 hours in the second step. The oxide molar ratio of the added silica sol to $Al_2O_3$, namely, $SiO_2/Al_2O_3$ was 0.10. The product powder was a pure 8-membered ring SAPO of chabazite structure, as confirmed by X-ray diffractometry, which detected no peak of AFI structure or the compound of JCPDS card No. 20-0045. It had a degree of crystallization of 1.00, and composed of crystal grains that were cubic and highly uniform both in size and shape. It had an average grain diameter of 1.9 μm. The resultant calcined powder had a Si/Al atomic ratio of the whole crystal grain of 0.15, surface Si/Al atomic ratio of 2.13 and surface Si/P atomic ratio of 3.01. Table 5 shows reaction performance 6 hours after the beginning of feed of raw materials. It is apparent from this example, that further incorporation of silica sol during the hydrothermal treatment gives a surface Si/Al atomic ratio higher than that of Example 16 which adopted the same hydrothermal treatment temperature of 170° C., and improves dimethylamine selectivity.

Comparative Example 11

A white calcined powder (85.0 g, catalyst yield: 80%) was prepared in the same manner as in Example 14, except that temperature as of the contents under hydrothermal treatment was elevated at 20° C./hour from 25 to 115° C., kept at 115° C. for 5 hours, and then elevated at 20° C./hour from 115 to 170° C. in the first step, and kept at 170° C. for 175 hours in part of crystallization step of the first step and in the second step. The product powder was a pure 8-membered ring SAPO of chabazite structure, as confirmed by X-ray diffractometry, which detected no peak of AFI structure or the compound of JCPDS card No. 20-0045. It had a degree of crystallization of 1.01, and composed of crystal grains which were cubic and highly uniform both in size and shape. It had an average grain diameter of 2.7 μm. The resultant calcined powder had a Si/Al atomic ratio of the whole crystal grain of 0.14, surface Si/Al atomic ratio of 2.26 and surface Si/P atomic ratio of 3.13. The crystal grains of the calcined powder had a 25 nm thick amorphous oxide layer, as observed by scanning transmission electron microscope. Table 5 shows reaction performance 6 hours after the beginning of feed of raw materials.

TABLE 4

| Examples | TEAOH/ $Al_2O_3$ molar ratio | $H_2O$/ $Al_2O_3$ molar ratio | Temperature and time for which the temperature is kept during the second step*1) | Degree of crystal-lization | Grain shape | Grain diameter (μm) | Thickness of amorphous oxide layer (nm) | Bulk Si/Al atomic ratio | Surface Si/Al atomic ratio | Surface Si/P atomic ratio |
|---|---|---|---|---|---|---|---|---|---|---|
| Example 12 | 0.95 | 75 | 170° C., 35 h | 1.00 | Cubic | 1.7 | — | 0.15 | 0.60 | 0.66 |
| Example 13 | 0.75 | 50 | 160° C., 35 h | 1.10 | Cubic | 1.7 | — | 0.14 | 1.07 | 1.24 |
| Example 14 | 0.75 | 50 | 170° C., 50 h | 1.05 | Cubic | 2.2 | 7 | 0.16 | 1.61 | 2.45 |
| Example 15 | 0.75 | 50 | 170° C., 100 h | 1.03 | Cubic | 2.4 | 13 | 0.15 | 1.98 | 2.92 |
| Example 16 | 0.75 | 75 | 170° C., 30 h | 1.00 | Cubic | 1.9 | — | 0.14 | 0.65 | 0.75 |
| Example 17 | 0.75 | 75 | 170° C., 30 h*2) | 1.00 | Cubic | 1.9 | — | 0.15 | 2.13 | 3.01 |
| Comparative Example 10 | 0.75 | 50 | 170° C., 5 h | 0.98 | Cubic | 2.5 | 25 | 0.14 | 0.49 | 0.53 |
| Comparative Example 11 | 0.75 | 50 | 170° C., 175 h | 1.01 | Cubic | 2.7 | 25 | 0.14 | 2.26 | 3.13 |

*1)Part of crystallization step in the first step is included.
*2)Silica sol was added at a stage of 170° C. and 20 hours.
TEAOH/$Al_2O_3$ molar ratio: Ratio of mole number of TEAOH to mole number of aluminum compound as $Al_2O_3$.
Degree of crystallization = Peak intensity at (100) plane of chabazite structure prepared in each example/peak intensity at (100) plane of the chabazite structure of Comparative Example 1.

Comparative Example 10

A white calcined powder (84.7 g, catalyst yield: 80%) was prepared in the same manner as in Example 14, except that temperature as of the contents under hydrothermal treatment was elevated at 20° C./hour from 25 to 115° C., kept at 115° C. for 5 hours, and then elevated at 20° C./hour from 115 to 170° C. in the first step, and kept at 170° C. for 5 hours in part of crystallization step of the first step and in the second step. The product powder was of pure chabazite structure, as confirmed by X-ray diffractometry, which detected no peak of AFI structure or the compound of JCPDS card No. 20-0045. It had a degree of crystallization of 0.98, and composed of crystal grains which were cubic and highly uniform both in size and shape. It had an average grain diameter of 2.5 μm. The resultant calcined powder had a Si/Al atomic ratio of the whole crystal grain of 0.14, surface Si/Al atomic ratio of 0.49 and surface Si/P atomic ratio of 0.53. The crystal grains of the calcined powder had a 2.5 nm thick amorphous oxide layer, as observed by scanning transmission electron microscopic analysis. Table 5 shows reaction performance 6 hours after the beginning of feed of raw materials.

TABLE 5

| Examples | Methanol conversion (wt %) | Monomethylamine selectivity (wt %) | Dimethylamine selectivity (wt %) | Trimethylamine selectivity (wt %) |
|---|---|---|---|---|
| Example 12 | 96 | 36 | 56 | 8 |
| Example 13 | 94 | 37 | 60 | 3 |
| Example 14 | 93 | 39 | 59 | 2 |
| Example 15 | 91 | 41 | 58 | 1 |
| Example 16 | 95 | 37 | 55 | 8 |
| Example 17 | 93 | 39 | 59 | 2 |
| Comparative Example 10 | 97 | 35 | 48 | 17 |
| Comparative Example 11 | 89 | 45 | 54 | 1 |

Reaction conditions: Temperature: 305° C., Pressure: 2 MPa, GHSV: 2500 $h^{-1}$

As apparent from these examples, it is found that the present 8-membered ring SAPO having a chabazite structure has an amorphous oxide layer on its crystal grain surface, and the oxide layer has a higher Si/Al atomic ratio than the whole crystal grain. It is also found that thickness of the amorphous oxide layer, and surface Si/Al and Si/P atomic ratios determined by X-ray photoelectron spectrometry are correlated to catalyst performance in production of methylamines by the reaction of methanol and ammonia. More specifically, methanol conversion and trimethylamine selectivity decrease while dimethylamine selectivity increases, as the thickness of the amorphous oxide layer or surface Si/Al or Si/P atomic ratio increases. It is found that an 8-membered ring SAPO of chabazite structure exhibiting high catalyst performance has an amorphous oxide layer of 3 to 20 nm in thickness, or 0.50 to 2.20 in surface Si/Al atomic ratio or 0.55 to 3.10 in surface Si/P atomic ratio, taking into account the balance between methanol conversion and dimethylamine selectivity. It is also found that rate at which the thickness or surface compositional ratio of the amorphous oxide layer changes during the hydrothermal treatment process depends upon TEAOH/$Al_2O_3$ or $H_2O$/$Al_2O_3$ molar ratio, and as time of the second hydrothermal treatment is prolonged, the thickness of the amorphous oxide layer increases, and the surface Si/Al and Si/P atomic ratios increase, thereby decreasing methanol conversion and trimethylamine selectivity. The catalyst prepared in Example 14 exhibited excellent catalyst life with 95 wt % in methanol conversion, 37 wt % in monomethylamine selectivity, 60 wt % in dimethylamine selectivity and 3 wt % in trimethylamine selectivity 1000 hours after the beginning of feed of raw materials under the conditions of reaction materials being fed at a space velocity (GHSV) of 1500 hour$^{-1}$, a temperature of 310° C. and a pressure of 2 MPa.

4. Relationship of Surface Composition and Thickness of Amorphous Oxide Layer with Catalyst Performance Concerning SAPO-56 and SAPO-17

Examples 18 and 19 and Comparative Example 12 deal with surface composition and thickness of the amorphous oxide layer and catalyst performance of SAPO-56 and SAPO-17 that have 8-oxygen-membered ring micropores. Table 6 summarizes Si/Al atomic ratio of the whole crystal grain (bulk Si/Al atomic ratio), surface Si/Al atomic ratio, surface Si/P atomic ratio and amorphous oxide layer thickness resulting from each of these examples. Reaction test was carried out in the same manner as in Examples 1 to 9.

Example 18

A uniform mixture of 85% by weight phosphoric acid (75.6 g), pure water (256.6 g) and N,N,N',N'-tetramethyl-1,6-hexanediamine (113.0 g) was supplemented with pseudoboehmite (43.1 g: PURAL NF from SASOL GERMANY GmbH, $Al_2O_3$ content: 77.5%) with stirring. This mixture was stirred for 1 hour, and then fumed silica (11.8 g: AEROSIL-200 from Nippon Aerosil Co., Ltd.) was added thereto, and further stirred for 30 minutes. The resulting mixture had a composition in terms of oxide molar ratio as follows: 2.0 TMHD:1.0 $Al_2O_3$:1.0 $P_2O_5$:0.6 $SiO_2$:50 $H_2O$ (TMHD: N,N,N',N'-tetramethyl-1,6-hexanediamine). The resulting mixture was hydrothermally treated with stirring in a stainless steel autoclave. In the hydrothermal treatment, temperature as of the contents was elevated at 20° C./hour from 25 to 115° C., kept at 115° C. for 5 hours and then elevated at 20° C./hour from 115 to 170° C. in the first step, and kept at 170° C. for 75 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 600° C. for 4 hours, to obtain white powder. The product powder was a pure SAPO-56 having 8-oxygen-membered ring micropores, as confirmed by X-ray diffractometry. The calcined powder had a Si/Al atomic ratio of the whole crystal grain of 0.27, surface Si/Al atomic ratio of 1.75 and surface Si/P atomic ratio of 2.71. The crystal grain of the calcined powder had a 10 nm thick amorphous oxide layer, as observed by scanning transmission electron microscope. Table 6 shows reaction performance 6 hours after the beginning of feed of raw materials.

Example 19

A uniform mixture of 85% by weight phosphoric acid (52.0 g), pure water (176.6 g) and quinuclidine (37.6 g) was supplemented with pseudoboehmite (29.7 g: PURAL NF from SASOL GERMANY GmbH, $Al_2O_3$ content: 77.5%) with stirring. This mixture was stirred for 1 hour, and then fumed silica (4.1 g: AEROSIL-200 from Nippon Aerosil Co., Ltd.) was added thereto, and further stirred for 30 minutes. The resulting mixture had a composition in terms of oxide molar ratio as follows: 1.5 Qn:1.0 $Al_2O_3$:1.0 $P_2O_5$:0.3 $SiO_2$:50 $H_2O$ (Qn: quinuclidine). The resulting mixture was hydrothermally treated with stirring in a stainless steel autoclave. In the hydrothermal treatment, temperature as of the contents was elevated at 20° C./hour from 25 to 115° C., kept at 115° C. for 5 hours and then elevated at 20° C./hour from 115 to 170° C. in the first step, and kept at 170° C. for 50 hours in part of crystallization step of the first step and in the second step, where hydrothermal treatment pressure was self-generated. The autoclave was cooled to room temperature and opened. The product slurry was centrifugally separated to obtain the precipitate, which was washed and centrifugally separated using 200 mL of pure water 3 times, and then dried at 80° C. for 12 hours. It was then calcined under air flow at 600° C. for 4 hours, to obtain white powder. The product powder was a pure SAPO-17 having 8-oxygen-membered ring micropores, as confirmed by X-ray diffractometry. The calcined powder had a Si/Al atomic ratio of the whole crystal grain of 0.11, surface Si/Al atomic ratio of 1.01 and surface Si/P atomic ratio of 1.36. The crystal grain of the calcined powder had a 5 nm thick amorphous oxide layer, as observed by scanning transmission electron microscope. Table 6 shows reaction performance 6 hours after the beginning of feed of raw materials.

Comparative Example 12

A white calcined powder was prepared in the same manner as in Example 18, except that temperature as of the contents under hydrothermal treatment was elevated at 20° C./hour from 25 to 115° C., kept at 115° C. for 5 hours, and then elevated at 20° C./hour from 115 to 170° C. in the first step, and kept at 170° C. for 5 hours in part of crystallization step of the first step and in the second step. The product powder was a pure SAPO-56 having 8-oxygen-membered ring micropores, as confirmed by X-ray diffractometry. The calcined powder had a Si/Al atomic ratio of the whole crystal grain of 0.25, surface Si/Al atomic ratio of 0.48 and surface Si/P atomic ratio of 0.51. The crystal grain of the calcined powder had a 2 nm thick amorphous oxide layer, as observed by scanning transmission electron microscope. Table 6 shows reaction performance 6 hours after the beginning of feed of raw materials.

As apparent from these examples, it is found that even an 8-membered ring SAPO of a structure other than chabazite structure has, on its crystal grain surface, the present amorphous oxide layer which has a higher Si/Al atomic ratio than the whole crystal grain. It is also found that these 8-membered ring SAPOs having an amorphous oxide layer of thickness or surface composition in a desired range exhibit excellent catalytic activity and dimethylamine selectivity in production of methylamines by the reaction of methanol and ammonia.

TABLE 6

| Surface Si/Al atomic ratio | Surface Si/P atomic ratio | Methanol conversion (wt %) | Monomethylamine selectivity (wt %) | Dimethylamine selectivity (wt %) | Trimethylamine selectivity (wt %) |
| --- | --- | --- | --- | --- | --- |
| 1.75 | 2.71 | 92 | 41 | 56 | 3 |
| 1.01 | 1.36 | 91 | 39 | 57 | 4 |
| 0.48 | 0.51 | 94 | 35 | 47 | 18 |

5. Examples of Disproportionation Reaction Using Monomethylamine as Starting Material Example 20 and Comparative Example 13 provide examples of disproportionation reaction using monomethylamine as a starting material.

Example 20

Reaction was carried out by feeding monomethylamine at a GHSV of 3000 hour$^{-1}$ to the reactor tube which was packed with 2.5 g (volume: 3.5 mL) of the catalyst prepared in Example 6 and kept at a reaction pressure of 2 MPa and a temperature of 320° C. Performance of disproportionation reaction from monomethylamine to ammonia and dimethylamine 6 hours after the beginning of the reaction was as follows:

Monomethylamine Conversion: 73% by mol,

Dimethylamine selectivity: 99% by weight, and

Trimethylamine selectivity: 1% by weight.

Comparative Example 13

Monomethylamine disproportionation reaction was carried out in the same manner as in Example 20, except that the catalyst prepared in Comparative Example 8 was used. Performance of the reaction 6 hours after the beginning thereof was follows:

Monomethylamine Conversion: 69% by mol,

Dimethylamine selectivity: 98% by weight, and

Trimethylamine selectivity: 2% by weight.

As shown in Example 20, the 8-membered ring SAPO having a chabazite structure of Example 6 also exhibited excellent performance in monomethylamine disproportionation reaction, compared with Comparative Example 13 in which the catalyst of Comparative Example 8, which was prepared following the Catalyst Preparation Example 1 described in Japanese Patent Laid-Open No. 2000-117114A, was used.

INDUSTRIAL APPLICABILITY

As apparent from the above description referring to the Examples and Comparative Examples, the 8-membered ring SAPO of the present invention has an amorphous oxide layer on its crystal grain surface, and the oxide layer has a higher silicon/aluminum atomic ratio than the whole crystal grain, and thus this molecular sieve exhibits higher catalytic activity and dimethylamine selectivity than the conventional techniques in production of methylamines on an industrial scale by, e.g., reaction of methanol and ammonia or disproportionation reaction of monomethylamine. Thickness and surface composition of the amorphous oxide layer, which have a great effect on catalyst performance, can be easily controlled by conditions for catalyst synthesis according to the present invention. Further, according to the present method for production of 8-membered ring SAPOs, those having high purity and degree of crystallization can be produced using a structure directing agent in a small amount that was conventionally impossible to attain. Thus, costs for raw materials and costs for waste disposal can be reduced more than conventional techniques, and hence the catalyst can be produced efficiently at a low cost. Moreover, the reduced amount of wastes contributes to reduce environmental load. Therefore, the 8-oxygen-membered ring micropore-containing crystalline silicoaluminophosphate molecular sieve, the method for producing the same, and the method for producing methylamines, all of which are provided by the present invention, are of great industrial value.

The invention claimed is:

1. A crystalline silicoaluminophosphate molecular sieve having 8-oxygen-membered ring micropores, which comprises an amorphous oxide layer on a crystal grain surface thereof, wherein the amorphous oxide layer has a higher atomic ratio of silicon to aluminum than the whole crystal grain thereof.

2. The crystalline silicoaluminophosphate molecular sieve having 8-oxygen-membered ring micropores, according to claim 1, wherein said whole crystal grain has an atomic ratio of silicon to aluminum in a range of 0.05 to 0.30, and said amorphous oxide layer on the crystal grain surface has an atomic ratio of silicon to aluminum of 0.50 or more, as determined by X-ray photoelectron spectroscopy.

3. The crystalline silicoaluminophosphate molecular sieve having 8-oxygen-membered ring micropores, according to claim 1 or 2, wherein said amorphous oxide layer on the crystal grain surface has an atomic ratio of silicon to phosphorus of 0.55 or more as determined by X-ray photoelectron spectroscopy.

4. The crystalline silicoaluminophosphate molecular sieve having 8-oxygen-membered ring micropores, according to claim 1, wherein said amorphous oxide layer on the crystal grain surface has a thickness in a range of 3 to 20 nm.

5. The crystalline silicoaluminophosphate molecular sieve having 8-oxygen-membered ring micropores, according to claim 1, which comprises at least one element selected from the group consisting of magnesium, yttrium, titanium, zirconium, manganese, iron, cobalt and tin.

6. The crystalline silicoaluminophosphate molecular sieve having 8-oxygen-membered ring micropores, according to claim 1, wherein said crystal grain has a rectangular parallelepiped and/or cubic form, and an average grain diameter of 5 μm or less.

7. The crystalline silicoaluminophosphate molecular sieve having 8-oxygen-membered ring micropores, according to claim 1, which has a crystal grain body portion that is the whole crystal grain from which said amorphous oxide layer on the crystal grain surface is excluded, said crystal grain body portion being of chabazite structure.

8. The crystalline silicoaluminophosphate molecular sieve having 8-oxygen-membered ring micropores of chabazite structure, according to claim 7, which has a ratio of peak intensity at (100) plane of AFI structure to peak intensity at (100) plane of chabazite structure, the ratio being 0.02 or less as determined by X-ray diffractometry.

9. A method for producing the 8-oxygen-membered ring micropore-containing crystalline silicoaluminophosphate molecular sieve defined in claim 1 by hydrothermally treating a starting mixture composed of an organic amine and/or organic ammonium salt together with an aluminum compound, phosphorus compound and silicon compound and water to produce the 8-oxygen-membered ring micropore-containing crystalline silicoaluminophosphate molecular sieve having an amorphous oxide layer on a crystal grain surface thereof, which comprises a first step for producing at least a crystalline portion thereof and a second step for conducting hydrothermal treatment to form the amorphous oxide layer on the crystal grain surface.

10. The method for producing the 8-oxygen-membered ring micropore-containing crystalline silicoaluminophosphate molecular sieve, according to claim 9, wherein said first step comprises two sub-steps for hydrothermal treatment, one being a step for carrying out hydrothermal treatment at 80 to 130° C. for 1 hour or more, and the other being a step for carrying out hydrothermal treatment at 150 to 200° C. for 1 to 10 hours.

11. The method for producing the 8-oxygen-membered ring micropore-containing crystalline silicoaluminophosphate molecular sieve, according to claim 10, wherein said sub-step of the first step for carrying out hydrothermal treatment at 80 to 130° C. for 1 hour or more includes a step in which temperature is increased from 80 to 130° C. in 1 hour or more, or a step in which temperature is kept at a constant level in a range of 80 to 130° C. for 1 hour or more.

12. The method for producing the 8-oxygen-membered ring micropore-containing crystalline silicoaluminophosphate molecular sieve, according to any one of claims 9 to 11, wherein said second step for hydrothermal treatment includes a step for carrying out hydrothermal treatment at 150 to 200° C. for 10 hours or more.

13. The method for producing the 8-oxygen-membered ring micropore-containing crystalline silicoaluminophosphate molecular sieve, according to claim 9, wherein said first step comprises two sub-steps, one being a step for carrying out hydrothermal treatment at a constant temperature in a range of 95 to 125° C. for 3 to 24 hours and the other being a step for carrying out hydrothermal treatment at 150 to 200° C. for 1 to 10 hours, and said second step for hydrothermal treatment comprises a step for carrying out hydrothermal treatment at 150 to 200° C. for 10 to 150 hours.

14. The method for producing the 8-oxygen-membered ring micropore-containing crystalline silicoaluminophosphate molecular sieve, according to claim 9, wherein said starting mixture composed of an organic amine and/or organic ammonium salt together with an aluminum compound, phosphorus compound, silicon compound and water has a ratio of the total mole number of the organic amine and organic ammonium salt to the mole number of the aluminum compound as $Al_2O_3$, the ratio being 0.4 to 0.98.

15. The method for producing the 8-oxygen-membered ring micropore-containing crystalline silicoaluminophosphate molecular sieve, according to claim 9, wherein said organic amine and/or organic ammonium salt is tetraethyl ammonium hydroxide.

16. The method for producing the 8-oxygen-membered ring micropore-containing crystalline silicoaluminophosphate molecular sieve, according to claim 9, wherein said aluminum compound is pseudoboehmite.

17. The method for producing the 8-oxygen-membered ring micropore-containing crystalline silicoaluminophosphate molecular sieve, according to claim 9, wherein said phosphorus compound is phosphoric acid.

18. The method for producing the 8-oxygen-membered ring micropore-containing crystalline silicoaluminophosphate molecular sieve, according to claim 9, wherein said silicon compound is silica sol.

19. The method for producing the 8-oxygen-membered ring micropore-containing crystalline silicoaluminophosphate molecular sieve, according to claim 9, wherein a silicon compound is further added before or during said second step.

20. The method for producing the 8-oxygen-membered ring micropore-containing crystalline silicoaluminophosphate molecular sieve, according to claim 9, wherein at least one element selected from the group consisting of magnesium, yttrium, titanium, zirconium, manganese, iron, cobalt and tin is further added.

21. The method for producing the 8-oxygen-membered ring micropore-containing crystalline silicoaluminophosphate molecular sieve, according to claim 9, wherein said 8-oxygen-membered ring micropore-containing crystalline silicoaluminophosphate molecular sieve is of chabazite structure.

22. A method for producing methylamines, comprising reacting methanol and ammonia in the presence of the 8-oxygen-membered ring micropore-containing crystalline silicoaluminophosphate molecular sieve defined in claim 1.

23. A method for producing methylamines, comprising reacting methanol and monomethylamine in the presence of the 8-oxygen-membered ring micropore-containing crystalline silicoaluminophosphate molecular sieve defined in claim 1.

24. A method for producing methylamines, comprising carrying out disproportionation reaction of monomethylamine in the presence of the 8-oxygen-membered ring micropore-containing crystalline silicoaluminophosphate molecular sieve defined in claim 1.

* * * * *